(12) United States Patent
Zehr et al.

(10) Patent No.: US 8,067,673 B2
(45) Date of Patent: Nov. 29, 2011

(54) METHODS FOR PLANT REGENERATION, TRANSFORMATION AND PRODUCTION OF INSECT RESISTANT TRANSGENIC OKRA

(75) Inventors: Usha Barwale Zehr, Jalna (IN); Madhavan Narendran Nair, Jalna (IN); Satish Govindrao Deole, Jalna (IN)

(73) Assignee: Maharashtra Hybrid Seeeds Company Ltd. (IN)

( * ) Notice: Subject to any disclaimer, the term of this patent is extended or adjusted under 35 U.S.C. 154(b) by 648 days.

(21) Appl. No.: 11/574,007

(22) PCT Filed: Aug. 16, 2005

(86) PCT No.: PCT/IN2005/000277
§ 371 (c)(1),
(2), (4) Date: Aug. 22, 2008

(87) PCT Pub. No.: WO2006/018857
PCT Pub. Date: Feb. 23, 2006

(65) Prior Publication Data
US 2009/0025099 A1    Jan. 22, 2009

(30) Foreign Application Priority Data
Aug. 20, 2004 (IN) .......................... 1522/DEL/2004

(51) Int. Cl.
*C12N 15/84* (2006.01)
*A01H 5/00* (2006.01)
*A01H 5/10* (2006.01)
*A01H 1/02* (2006.01)

(52) U.S. Cl. ........ 800/294; 800/279; 800/300; 800/302; 800/303; 435/430; 435/431

(58) Field of Classification Search ........................ None
See application file for complete search history.

(56) References Cited

FOREIGN PATENT DOCUMENTS
WO    WO 02/072849    9/2002

OTHER PUBLICATIONS

Roy et al. Plant Science 60(1): 77-81 (1989).*
Gassama-Dia et al. African Journal of Biotechnology 3(4): 226-228 (Apr. 2004).*
Srivatanakul et al. Journal of Plant Physiology 158(2): 255-260 (2001).*
Sen et al. Indian Journal of Textile Research 12: 152-153 (1987).*
Nair et al. Agricultural Research Journal of Kerala 14(2): 171-172 (1976).*
Haberlandt, G., "Theoretically All Plant Cells Are Able to Give Rise to A Complete Plant", (1902) Kulturversuche mit isolierten Pflanzenzellen. Sitzungsber. Akad. Wiss. Wien. Math.-Naturwiss. Kl., Abt. 111, 69-92.
Chilton, Mary-Dell, "A Vector for Introducing New Genes into Plants", Scientific American (1983) 248.6:36-45.
Mangat, B. S. et al., "Tissue Culture and Plant Regeneration of Okra (*Abelmoschus Esculentus*)", Plant Science (1986), 47:57-61.
Roy, M. K. et al., "Regeneration of Plants From Callus Tissue of Okra (*Abelmoschus Esculentus*)", Plant Science (1989), 60:77-81.
Murai, Norimoto, et al., "Phaseolin Gene From Bean is Expressed After Transfer to Sunflower Via Tumor-Inducing Plasmid Vectors", Science (1983), 222:476-482.
Fraley, Robert T., et al., "Expression of Bacterial Genes in Plant Cells", Proc. Natl. Acad. Sci. USA (1983) 80:4803-4807.
Lorz, Horst, et al., "Gene Transfer to Cereal Cells Mediated by Protoplast Transformation", Mol. Gen. Genet., (1985) 199:178-182.
Potrykus, Ingo, et al., "Direct Gene Transfer to Cells of a Graminaceous Monocot", Mol. Gen. Genet., (1985) 199:183-188.
Crossway, Anne et al., "Integration of Foreign DNA Following Microinjection of Tobacco Mesophyll Protoplasts", Mol. Gen. Genet., (1986) 202: 179-185.
Fromm, Michael, et al., "Expression of Genes Transferred into Monocot and Dicot Plant Cells by Electroporation", Proc. Natl. Acad. Sci. USA (1985) 82:5824-5828.
Fromm, Michael E., et al., "Stable Transformation of Maize after Gene Transfer by Electroporation", Nature (1986) 319:791-793.
De Block, Marc et al., "Expression of Foreign Genes in Regenerated Plants and in Their Progeny", The EMBO Journal (1984) 3:1681-1689.
Horsch, R. B., et al., "A Simple and General Method for Transferring Genes into Plants", Science (1985) 227:1229-1231.
Klein, T. M., et al., "High-Velocity Microprojectiles for Delivering Nucleic Acids into Living Cells", Nature (1987) 327:70-73.
Klein, Theodore M., et al., "Transformation of Microbes, Plants and Animals by Particle Bombardment", Bio/ Technology (1992) 10:286-292.
Casas, Ana M., et al., "Transgenic Sorghum Plants Via Microprojectile Bombardment", Proc. Natl. Acad. Sci. USA (1993) 90:11212-11216.
Yoder, John I., et al., "Transformation Systems for Generating Marker-Free Transgenic Plants", Bio/Technolgoy (1994) 12:263-267.
Komari, Toshihiko et al., "Vectors Carrying Two Separate T-DNAs for Co-Transformation of Higher Plants Mediated by *Agrobacterium Tumefaciens* and Segregation of Transformants Free From Selection Markers", The Plant Journal (1996) 10:165-174.
Fischhoff, David A., et al., "Insect Tolerant Transgenic Tomato Plants", Bio/Technology (1987) 5:807-813.
Johnson, Russell, et al., "Expression of Proteinase Inhibitors I and II in Transgenic Tobacco Plants: Effects on Natural Defense Against *Manduca Sexta* Larvae", Proc. Natl. Acad. Sci. USA (1989) 86:9871-9875.

(Continued)

Primary Examiner — David T Fox
(74) Attorney, Agent, or Firm — Lowe Hauptman Ham & Berner, LLP

(57) ABSTRACT

The present description concerns methods for regeneration of whole plant from the explants obtained from the *Abelmoschus* species preferably *A. esculentus*. In addition the present description also concerns methods for transforming okra plant, plant cells and tissues either with the use of recombinant *Agrobacterium* strain or by bombarding the explants with tungsten or gold particles coated with DNA sequences of interest. An efficient method to isolate embryos from imbibed seeds of okra is also described which enables the use of young meristematic cells of plumule tip for efficient regeneration and transformation of okra plants. Further, transformed okra plants, plant cells and tissues for improved agronomic/non agronomic traits and insect resistance are produced either by using marker based or marker free systems.

26 Claims, 4 Drawing Sheets

OTHER PUBLICATIONS

Figure 1:
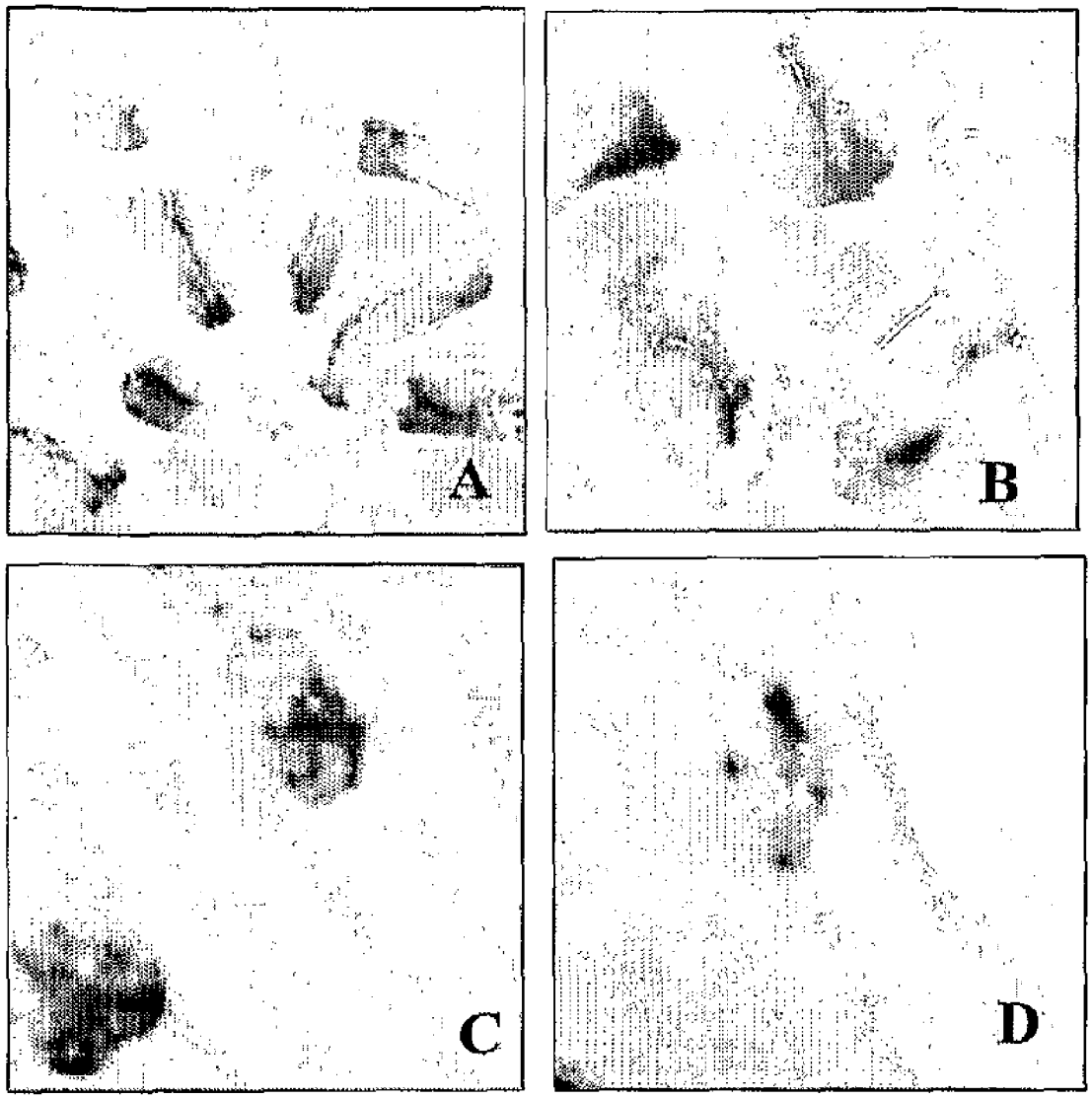

Murashige, T., et al., "A Revised Medium for Rapid Growth and Bioassays With Tobacco Tissue Cultures", Physiol. Plant. (1962) 15:473-497.

Gamborg, O. L., et al., "Nutrient Requirements of Suspension Cultures of Soybean Root Cells", Exp. Cell Res. (1968) 50: 151-158.

Sanford, John C., "The Biolistic Process", Trends in Biotechnology, (1988) 6:299-302.

Sanford, J. C., et al., "An Improved, Helium-Driven Biolistic Device", Technique J. Methods Cell Mol. Biol. (1991) 3:3-16.

Kikkert, Julie Russell, "The Biolistic® PDS-1000/He Device", Plant Cell, Tissue and Organ Culture (1993) 33:221-226.

Jefferson, Richard A., et al., "β-Glucuronidase from *Escherichia Coli* as a Gene-Fusion Marker", Proc. Natl. Acad. Sci. USA (1986) 83: 8447-8451.

Siddiqua, Mahbuba Khatoon, Thesis: "Further Characterization of Okra Mosaic Virus and Tissue Culture of *Abelmoschus Escul Entus*", Sep. 28, 2001, XP-002389665.

International Preliminary Examination Report dated Jan. 16, 2007 from corresponding application No. PCT/IN2005/000277.

International Search Report from corresponding application No. PCT/IN20051000277. Aug. 2006.

\* cited by examiner

Figure: 2

METHODS FOR PLANT REGENERATION, TRANSFORMATION AND PRODUCTION OF INSECT RESISTANT TRANSGENIC OKRA

RELATED APPLICATIONS

The present application is a National Phase entry of International Application Number PCT/IN2005/000277, filed Aug. 16, 2005, which claims priority from Indian Application No. 1522/DEL/2004, filed Aug. 20, 2004, the disclosures of which are hereby incorporated by reference herein in their entirety.

1. TECHNICAL FIELD

The present invention provides novel methods of regeneration of whole plant from explants of okra plant and other *Abelmoschus* species. Further, the invention also provides methods for transformation of plant, plant cells and tissues of *Abelmoschus* species either using the *Agrobacterium* mediated method or the particle bombardment method. Transgenic insect resistant okra plants were generated, either by using marker based systems or marker-free systems.

2. BACKGROUND AND PRIOR ART REFERENCES

2. A. Okra.

Okra (*Abelmoschus esculentus*) is one of the most important vegetable crops. The fruits are consumed in various forms in a number of countries. Okra has also been used as a source of fiber and for the production of oil and proteins.

Okra is susceptible to many insect pests and diseases which reduce the yield across the Okra growing regions. Okra yellow vein mosaic virus is a devastating disease in India and many other countries. This crop is extensively damaged by the Lepidopteran insect/pests viz.; Shoot and fruit borer (*Earias vitella, E. insulana*) and the Fruit borer (*Helicoverpa armigera*). Genetic improvement by conventional plant breeding is impaired due to the lack of resistance sources to pests and diseases in Okra germplasm.

2. B. Plant Cell and Tissue Culture

Each plant cell has the inherent ability for independent development into a whole organism if provided with the proper external conditions. Since the early demonstration of this ability, viz., totipotency and differentiation in vitro, plant tissue culture techniques have been widely used in the clonal multiplication of plants (Herberlandt., Sber. Akad. Wiss. Wien. (1902) 111:69-92).

Plant tissue culture technology is making significant contributions to agriculture in the clonal propagation, haploid breeding, mutant cultures, pathogen free plants, cryopreservation of plant tissues for the establishment of in vitro gene banks, production of secondary products and genetic engineering of plants (Chilton., Scientific American (1983) 248.6: 36-45).

The prospects of success with the genetic engineering of plants have created considerable public interest. This technique involves the insertion of foreign genes into plant cells using vectors and the regeneration of whole plants from transformed single cells using plant tissue culture techniques. Although tissue culture based plant regeneration methods have been standardized for a wide variety of plant species, many crops have been recalcitrant and thus restricts the genetic engineering potential of these plants.

2. C. Tissue Culture of Okra

Tissue culture based direct plant regeneration of okra has been described by Mangat and Roy., Plant Science (1986) 47:57-62. This investigation outlines the comparative tissue culture responses of hypocotyl, cotyledon, cotyledonary node and primary leaf explants aseptically grown okra seedlings cultured on 6 different media. The plant regeneration was not attained from hypocotyl and leaf segment explants in all the 6 media tested. The cotyledon explants responded moderately in plant regeneration, on one out of 6 media tested. Cotyledon node explants did not regenerate on 3 of the media, whereas, responded low in shoot regeneration on 1 medium, and responded very high in the shoot regeneration on another medium.

In the above publication the shoot regeneration frequency is mentioned as nil, low, moderate and very high and not in figures (%). It makes the comparison of regeneration frequency, difficult.

In a second publication, Roy and Mangat (Roy et al., Plant Science (1989) 60:77-82) have reported the regeneration of plants from cotyledonary-axil derived callus tissue of Okra. Callus induction that resulted from all the explants cultured on MS medium supplemented with the benzyl adenine (BA). The hypocotyl-derived callus remained non-organogenic, whereas, cotyledonary-axil-derived callus produced shoots. The addition of silver nitrate in media resulted in up to 74% of the bud primordia going onto produce shoots.

The study of prior art shows no method available for the regeneration of plants from plumule of embryo. Our present inventions describe methods for the high efficiency plant regeneration from plumule of okra for the first time.

The study of prior art also shows no method available for the regeneration of plants from the other explants also tested during in our investigation.

2. D. Plant Transformation and Generation of Transgenic Plants

The development of gene transfer techniques for plant species is of great interest, importance and value because it can be used for the transfer of beneficial genes of interest into plants.

A variety of techniques have been used to introduce foreign genes into plant cells. *Agrobacterium* mediated transformation has been described by Murai et al., Science (1983) 222: 476-482, Fraley et al., Proc. Natl. Acad. Sci. USA (1983) 80:4803-4807; Direct DNA uptake method has been described by Lorz et al., Mol. Gen. Genet., (1985) 199:178-182, Portrykus et al., Mol. Gen. Genet., (1985) 199:183-188; Microinjection method has been described by Crossway et al., Mol. Gen. Genet., (1986) 202:179-185; High velocity micro-projectile method has been described by Klein et al., Nature (1987) 327:70-73 and Electroporation method has been described by Fromm et al., Proc. Natl. Acad. Sci. USA (1985) 82:5824-5828, Fromm et al., Nature (1986) 319:791-793.

2. E. *Agrobacterium*-Mediated Transformation

One of the most common methods of introducing foreign genes into plant cells is through *Agrobacterium*-mediated transformation. *Agrobacterium* is a natural plant pathogen and it mediates genetic transformation as part of the natural process it utilizes when it infects a plant cell. During the process of transformation a specific segment of the vector which is known as T-DNA, is transferred into the cells. The T-DNA of *Agrobacterium* can be engineered to contain gene/s or DNA sequences of interest that can be transferred into the host plant cells and inserted into the plant genome.

*Agrobacterium*-mediated transformation is attractive because of the ease of the protocol coupled with minimal equipment costs. Moreover, transgenic plants obtained by this method often contain a single copy of T-DNA integrations.

*Agrobacterium*-mediated transformation and the subsequent regeneration of transgenic plants carrying inserted genes were described by Murai et al., Science (1983) 222: 476-482. Fraley et al., Proc. Natl. Acad. Sci. USA (1983) 80:4803-4807. De Block et al., The EMBO Journal (1984) 3:1681-1689 and Horsch et al., Science (1985) 227:1229-1231.

2. F. Biolistic-Mediated or Particle Bombardment Method of Transformation

Another common method of introducing foreign gene/s into plant cells is using particle bombardment which is also known as biolistic or high velocity microprojectile. The basis of particle bombardment is the acceleration of particles coated with gene/s of interest toward cells, resulting in the penetration of the protoplasm by the particles and subsequent expression of the introduced gene/s. In this method helium pressure is used to accelerate particles coated with DNA into the cells.

Microprojectile bombardment can transform diverse target tissues. Particle bombardment and subsequent regeneration of transgenic plants carrying inserted genes were described by Klein et al., Nature (1987) 327:70-73. Klein et al., Bio/Technology (1992) 10:286-292. Casas et al., Proc. Natl. Acad. Sci. USA (1993) 90: 11212-11216.

2. G. Transformation of Okra

The study of prior art shows no method available for the transformation of Okra plant, cells and tissues. Our present inventions describe methods for the transient and stable transformation of okra plant, cells and tissues using *Agrobacterium*-mediated and biolistic transformation systems for the first time.

2. H. Marker Based Transformation Systems

In the marker based transformation system, the gene of interest and the selectable marker gene (Eg. NPT II gene) are linked. In the marker based *Agrobacterium*-mediated transformation system, the T-DNA is engineered to contain the gene of interest and the marker gene. Where as in the marker based biolistic transformation system the plasmid used, contains the gene of interest and the selectable marker gene. The transgenic plants generated from the above systems contain the marker gene along with the gene of interest.

2. I. Marker-Free Transformation Systems

Marker-free transformation systems have the advantages of introducing agronomical important genes, and at the same time, avoiding the introduction of the selectable marker genes. Different methods have been employed for the generation of marker-free transgenic plants. These methods include *Agrobacterium*-mediated co-transformation, excision of the selectable marker via crellox recombination, use of transposable elements, co-bombardment of the plasmids and altered metabolism (Yoder et al., Bio/Technology (1994) 12:263-267).

*Agrobacterium*-mediated co-transformation, using two separate plasmids in a single *Agrobacterium*, i.e. one vector carrying the selectable marker gene in one T-DNA and the other vector carrying the gene of interest in another T-DNA are used. The transgenic plants generated from this transformation system are analyzed and the plants having gene of interest but with out selectable marker gene are selected in the further generations from the segregated progenies (Komori et al., The Plant Journal (1996) 10: 165-174).

2. J. Engineering Plants for Insect Resistance

2. J. A. *Bacillus thuringiensis* (Bt) gene

*Bacillus thuringiensis* (Bt) is a gram positive bacterium which produces a variety of insecticidal crystal proteins toxic to insects. These Bt genes have been successfully engineered into crop plants to get resistance to the specific insect pests in a number of crops. For example insect resistant transgenic tomato plants were generated with Bt gene by Fischhoff et al., Bio/Technology (1987) 5:807-813.

2. J. B. Protease Inhibitors

Protease inhibitors are an important element of plant defense response to insect predation. Transgenic plants expressing protease inhibitors show enhanced resistance to predation by pests, indicating the useful function of these inhibitors (Johnson et al., PNAS (1990) 86:9871-9875.

2. K. Insect Bioassays

The bioassays using specific insect pests with plants/plant parts are conducted to understand the resistance or susceptibility of the plant towards the pest. The efficacy of the specific insect resistant protein expressed in transgenic plants is tested with the specific target pest in the insect bioassays. The resistance of the plant towards specific target pests is compared with non-transgenic plant controls.

3. OBJECTS OF THE INVENTION

An object of the present invention is to provide methods for regeneration of okra plant and *Abelmoschus* species.

Another object of the present invention is to provide methods for transformation of okra plant, plant cells and tissues.

Still another object of the present invention is to provide methods to transform okra plant, plant cells and tissues by co-cultivating the explants with recombinant *Agrobacterium* strain comprising DNA/RNA sequences of interest.

Still another object of the present invention is to provide methods to transform okra plant, plant cells and tissues by bombarding the explants with tungsten or gold particles coated with DNA sequence of interest.

Further, another object of the present invention is to obtain okra plant, plant cells and tissues which carry and/or confer the traits of agronomic and non-agronomic importance.

Still another object of the present invention is to obtain okra plant, plant cells and tissues which confer tolerance or resistance to disease, herbicide or insects.

Still another object of the present invention is to obtain marker-free, transgenic, okra plants.

Still another object of the present invention is to obtain marker-free, transgenic insect resistant okra plants.

4. SUMMARY OF THE INVENTION

The present invention provides novel and efficient methods of regeneration of whole plant of *Abelmoschus* species preferably *A. esculentus*.

Another aspect of the present invention is to provide methods for regeneration of whole plant of *Abelmoschus* species wherein the explants are selected from a group consisting of cotyledon with petiole, hypocotyls, embryo, immature embryo, leaf lamina, cotyledonary axil, shoot tip, anther, root, callus or other suitable explants.

The invention provides for a method of regeneration of the explants wherein the explants are cultured on a regeneration medium (MS0Z$_2$ medium) containing a cytokinin preferably Zeatin in the range 0.01 to 5 mg/l, preferably 2 mg/l. The explant can also be regenerated on other media known in the art having a combination of cytokinins in the range of 0.01 to 20 mg/l or combination of cytokinins and auxin, with the latter in the range of 0.01 to 5 mg/l.

Further, the explants are incubated at a temperature of 18° C. to 30° C., preferably 26° C. and luminosity of 250 to 5000 lux for the regeneration of multiple shoot buds. The invention also provides for further multiplication of shoot buds on the medium as described above.

The invention also provides a method wherein the multiplied shoot buds are further transferred to a medium without growth regulator (MS0 medium) or medium with low concentration of auxin in the range of 0.01 to 2 mg/l for further elongation of shoot and the induction and growth of roots to obtain plantlets.

In another aspect of the invention, the plantlet obtained is phenotypically normal and fertile and is capable of producing the fertile seeds in subsequent generations.

In another aspect of the invention, the plantlet obtained is a mutant and fertile and is capable of producing the fertile seeds in subsequent generations The present invention also provides a novel and efficient methods for transforming plant, plant cells and tissues of *Abelmoschus* species using *Agrobacterium*-mediated or particle bombardment methods.

Different varieties or accessions of *Abelmoschus esculentus* species are selected for transforming plant, plant cells and tissues using *Agrobacterium*-mediated or particle bombardment methods.

In another aspect of the invention the explants for transformation are selected from a group consisting of cotyledon with petiole, hypocotyls, embryo, immature embryo, leaf lamina, cotyledonary axil, shoot tip, anther, root and callus or any other suitable explants.

Another aspect of the present invention is to devise an efficient method to isolate embryos from imbibed seeds of okra which enables the use of young meristemic cells of plumule end for transformation.

Another aspect of this invention is to provide a method of wounding to increase transformation efficiency. The wounding involved pricking or penetrating the embryo and other explants by a sharp object, a needle or an abrasive object.

Further the transformed explants are cultured on medium containing a cytokinin, preferably Zeatin, in the range 0.01 to 5 mg/l, preferably 2 mg/l (MS0Z$_2$H$_{10}$C medium) or a combination of cytokinins in the range of 0.01 to 20 mg/l or combination of cytokinins and auxin, with the latter in the range of 0.01 to 5 mg/l, containing antibiotic hygromycin in the range of 5 mg/l to 100 mg/l, preferably 10 mg/l for selection of transformed plant cells and tissues and for the generation of multiple shoot buds.

Further the transformed and multiplied shoot buds are transferred on shoot elongation media as described above and then in another media for induction and growth of roots to obtain whole plants.

Another aspect of the present invention is to provide a methods for transforming plant, plant cells and tissues of *Abelmoschus* species using *Agrobacterium*-mediated or particle bombardment methods wherein the transformed okra plant carry the DNA/RNA sequence of interest wherein the transformed plant shows improved agronomic traits or a combination of traits comprising for yield, drought resistance, stress resistance, nutritional value, inducing male sterility into the plant, cells and tissues.

Another aspect of the present invention is to provide a methods for transforming plant, plant cells and tissues of *Abelmoschus* species using *Agrobacterium*-mediated or particle bombardment methods wherein the transformed okra plant carry the DNA/RNA sequence of interest wherein the transformed plant shows tolerance or resistance to disease, herbicide or insects.

Another aspect of the present invention is to provide a method of generating marker-free, transgenic okra plants, with a nucleotide sequence of interest.

Another aspect of the present invention is to provide transformed okra plants showing tolerance or resistance to disease, herbicide or insects

5. BRIEF DESCRIPTION OF ACCOMPANYING DRAWINGS

FIG. 1: Transformed mature embryo, cotyledonary axil, shoot tip and callus by *Agrobacterium*-mediated method showing GUS activity.

Figure 2:
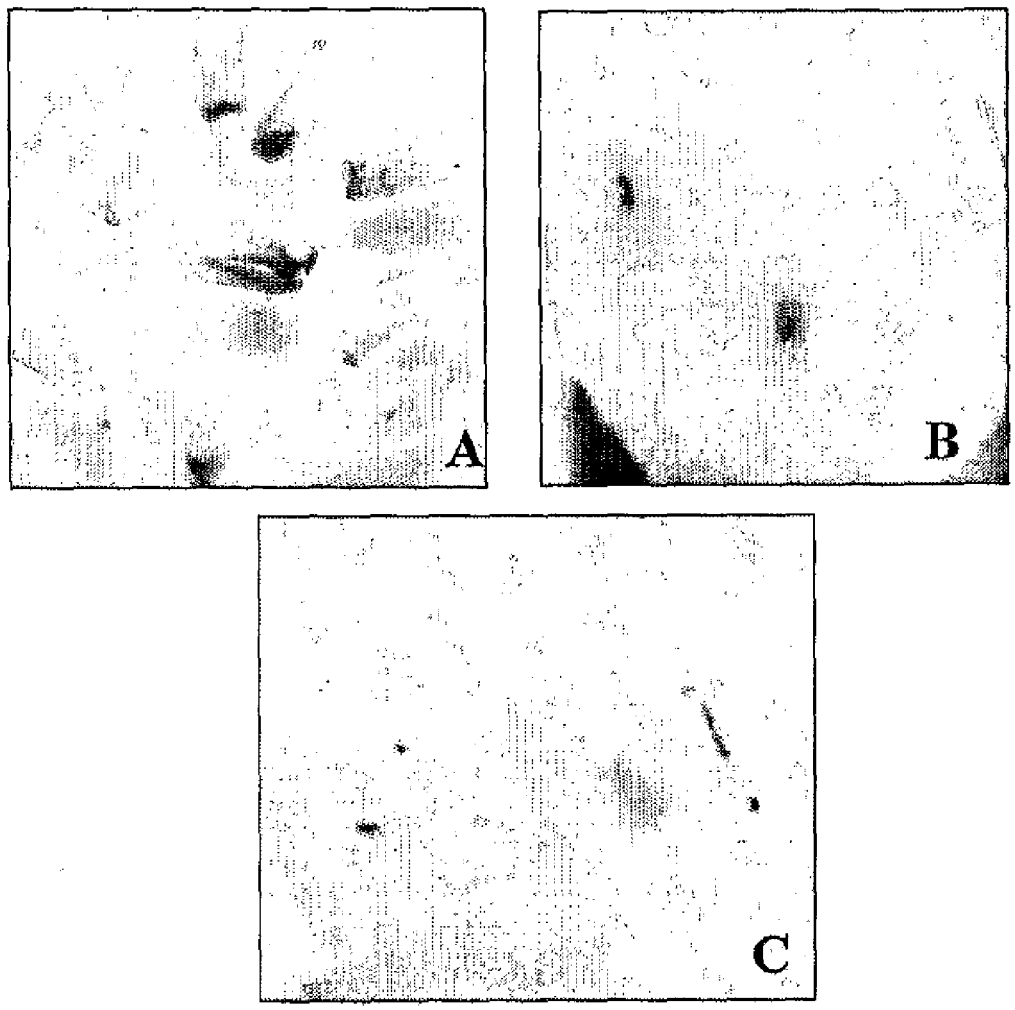

FIG. 2: Transformed mature embryo, callus and by anther Biolistic-method showing GUS activity.

Figure 3:
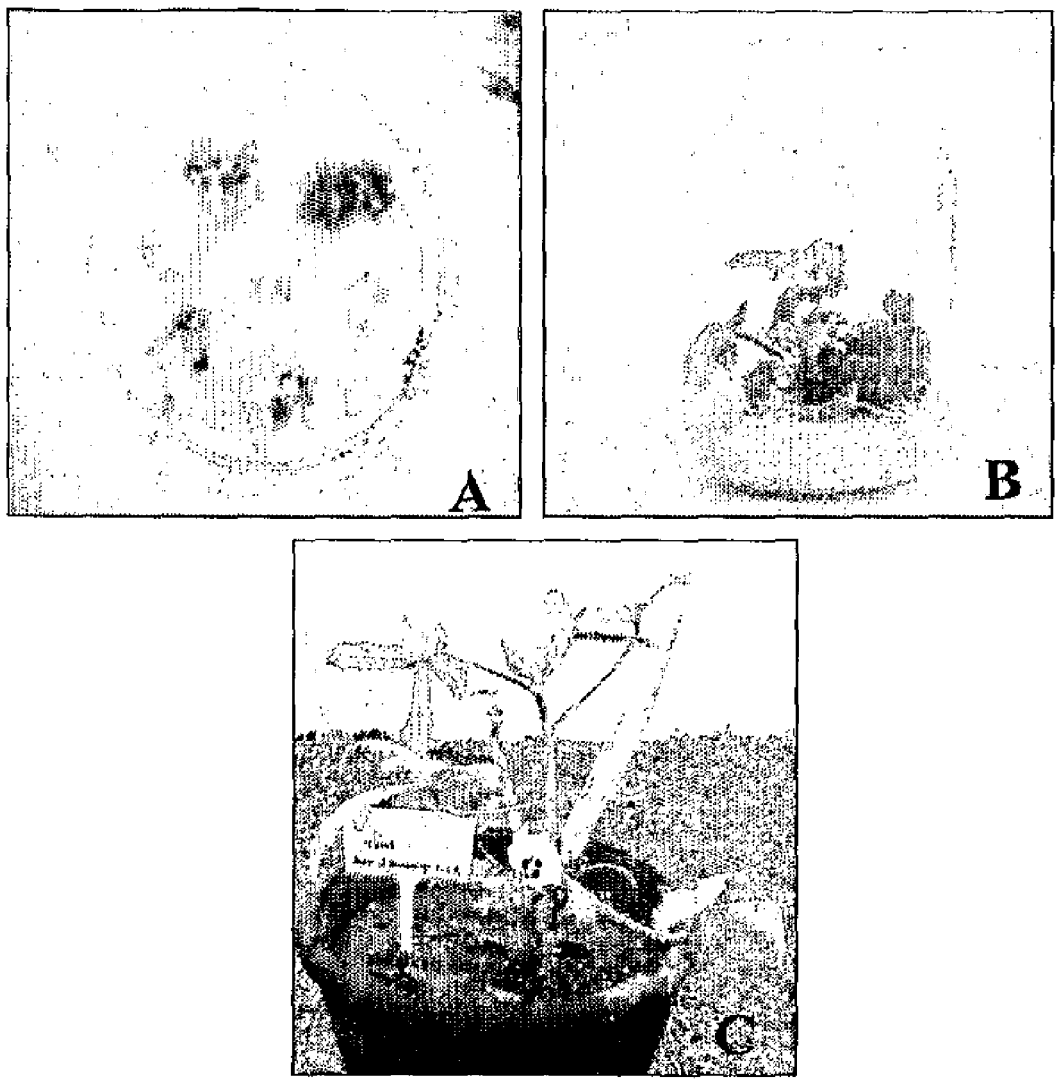

FIG. 3: A) Multiple shoot buds developed from the plumule tip of the embryo.
B) Elongated shoots and Rooting of regenerated okra plant.
C) Hardened okra plant in green house showing fruiting FIG. 4: Transformed seedlings of T1 generation showing GUS activity.

6. DETAILED DESCRIPTION OF THE INVENTIONS

An embodiment of the present invention is to provide a method of regenerating whole plant from explants of *Abelmoschus esculentus* species, wherein the said method comprising the steps of:
a) surface sterilizing the seeds and imbibing the seeds in water
b) germinating the surface sterilized seeds of step (a) on a suitable culture media to obtain seedlings,
c) obtaining the explants from step (a) or step (b),
d) wounding the explants from step (c),
e) culturing the explants of step (c), on a suitable medium to obtain multiple shoot buds or callus
f) culturing the shoot buds of step (e) on a suitable medium for further elongation of shoots and induction of roots to obtain rooted plantlets
g) Transferring the rooted plantlets of step (f) in soil, to obtain fertile R$_0$ plants,
h) Advancing the plants of step (g) to subsequent generations.

Further, the invention provides for regeneration of plants from *Abelmoschus* species wherein the species are selected from a group consisting of *A. caillei, A. moschatus, A. manihot, A. tuberculatus, A. ficulneus, A. crinitus, A. angulosus A. tetraphyllus*.

Another embodiment of the present invention provides a method of regeneration of okra plant, wherein the surface sterilized seeds are washed and imbibed for a period of 0 to 48 hours, and then placed on MS0 medium for germination [MS0 medium contains MS salts, B5 vitamins, 0.8% agar, 3% sucrose and pH 5.8]

Further, the invention provides for use of various explants for regeneration of okra plant wherein the explants are selected from a group consisting of cotyledon with petiole, hypocotyls, embryo, immature embryo, leaf lamina, cotyledonary axil, shoot tip, anther, root, callus or other suitable explants.

Still another embodiment of the present invention is to provide a method of regeneration of okra plant wherein the surface sterilized and imbibed seeds are used to isolate the embryos in sterile conditions by pressing with tweezers or any other means and these embryos are washed in sterile water and blotted dry on filter paper and later placed on soaked sterile filter paper.

Another embodiment of the present invention is to provide a method of regeneration of okra plant wherein the explants are transferred onto a medium containing Zeatin in the range 0.01 to 5 mg/l, preferably 2 mg/l ($MS0Z_2$ medium). The explants are placed for incubation in plant tissue culture incubation room at a temperature 18° C. to 30° C. (preferably 26° C.) and luminosity of 250 to 5000 lux for the regeneration of multiple shoot buds. The explants may also be regenerated using other media compositions known in the art such as media containing a combination of cytokinins in the range of 0.01 to 20 mg/l or combination of cytokinins and auxin, with the latter in the range of 0.01 to 5 mg/l.

Another embodiment of the present invention is to provide a method of regeneration of okra plant wherein the multiple shoot buds regenerated are excised and transferred onto a medium containing a cytokinin preferably Zeatin in the range 0.01 to 5 mg/l, preferably 2 mg/l ($MS0Z_2$ medium) or a combination of cytokinins in the range of 0.01 to 20 mg/l or combination of cytokinins and auxin, with the latter in the range of 0.01 to 5 mg/l, and kept for incubation for the further multiplication of shoot buds.

Another embodiment of the present invention is to provide a method of regeneration of okra plant wherein the said shoot is transferred onto medium and allowed to grow to a length of 0.5 cm to 7 cm, preferably 1.5 cm.

Another embodiment of the present invention is to provide a method of regeneration of okra plant wherein, the elongated shoot is transferred to a medium without growth regulator (MS0 medium) or medium with low concentration of auxin in the range of 0.01 to 2 mg/l for further elongation of shoot and the induction and growth of roots to obtain plantlets.

Another embodiment of the present invention is to provide a method of regeneration of okra plant wherein the plantlet is transferred in soil for further growth. The regenerated plantlet grown is phenotypically normal and/or mutant and fertile and is capable of producing fertile seeds in subsequent generations. Further the invention provides for advancing the generation of the regenerated Okra plants.

Still another embodiment of the present invention is to provide a method for transforming *Abelmoschus* species, wherein the said method comprising the steps of
  a) surface sterilizing the seeds, and imbibing the seeds with water,
  b) germinating the seeds of step (a) in a suitable culture medium to obtain seedlings,
  c) obtaining the explants from step (a) or step (b),
  d) wounding the explants of step (c),
  e) co-cultivating the explants of step (d) with recombinant *Agrobacterium* strain,
  f) culturing the explants of step (e) on a suitable tissue culture medium to select transformed plant cells and tissues,
  g) culturing the transformed plant cells and tissues of step (f) on a suitable tissue culture medium to obtain shoot buds, and
  h) culturing the shoot buds of step (g) in a suitable rooting medium to obtain rooted transformed plants.

Further, the invention provides for regeneration of plants from *Abelmoschus* species wherein the species are selected from a group consisting of *A. caillei A. moschatus, A. manihot, A. tuberculatus, A. ficulneus, A. crinitus, A. angulosus A. tetraphyllus*.

Another embodiment of the present invention is to provide a method wherein the surface sterilized seeds are washed and imbibed in water for a period of 0 to 48 hours. Further, the surface sterilized seeds are placed on MS0 medium for germination (MS0 medium contains MS salts, B5 vitamins, 0.8% agar, 3% sucrose and pH 5.8)

Still another embodiment of the present invention is to provide a method for transforming *Abelmoschus esculentus* species, wherein the surface sterilized seeds are used to isolate the embryos in sterile conditions by pressing with tweezers or any other means and these embryos are washed in sterile water and blotted dry on filter paper and later placed on soaked sterile filter paper.

Another embodiment of the present invention is to provide a method for transforming *Abelmoschus* species, wherein the explants are selected from a group consisting of cotyledon with petiole, hypocotyls, embryo, immature embryo, leaf lamina, cotyledonary axil, shoot tip, anther, root and callus or other suitable explants.

Another embodiment of the present invention is to provide a method wherein the embryos or various explants of *Abelmoschus* species are wounded with a sterile needle or with any suitable sharp object.

Another embodiment of the present invention is to provide a method for transforming *Abelmoschus* species, wherein the recombinant *Agrobacterium* strain carrying DNA/RNA sequence comprises of a coding or non-coding gene sequence, inclusive or not, of terminator or promoter, as an expressing or non-expressing cassette.

Further, the *Agrobacterium* strain carrying DNA/RNA sequences confers improved agronomic traits or combination of traits comprising for yield, drought resistance, stress resistance, nutritional value or inducing male sterility into the plant, cells and tissues.

Another embodiment of the present invention is to provide methods for transforming *Abelmoschus* species, wherein the DNA/RNA sequences confers tolerance or resistance to disease, herbicide or insects to transformed plant, cells and tissues.

Another embodiment of the present invention is to provide a method for transforming *Abelmoschus* species, wherein the DNA/RNA sequences are either coding or non coding sequences.

Another embodiment of the present invention is to provide methods for the transformation of okra using marker-free systems.

Further, the explant is inoculated with the recombinant *Agrobacterium* strain containing DNA sequence of interest. The explant is blotted dry on sterile filter paper and transferred onto co-cultivation medium. Various media combinations may be used for co-cultivation medium which is selected from a group consisting of MS0 medium or MS0As medium or $MS0Z_2$ medium or $MS0Z_2As$ medium.

The said medium $MS0Z_2$ or $MS0Z_2As$ contains a cytokinin, preferably Zeatin, in the range 0.01 to 5 mg/l, preferably 2 mg/l ($MS0Z_2$ medium).

Further, the explant after co-cultivation is washed with liquid MS0 medium with 500 mg/l Cefotaxime or suitable antibiotic to kill *Agrobacterium*.

Another embodiment of the present invention is to provide a method for transforming *Abelmoschus* species, wherein the said explant is blotted dry on sterile filter paper and can be cultured on a various media known in prior art as medium containing a cytokinin, preferably Zeatin, in the range 0.01 to 5 mg/l, preferably 2 mg/l (($MS0Z_2H_{10}C$ medium) or a combination of cytokinins in the range of 0.01 to 20 mg/l or combination of cytokinins and auxin, with the latter in the range of 0.01 to 5 mg/l, containing antibiotic for selection of transformed plant cells and tissues. Further the said explant is incubated in plant tissue culture incubation room with temperature 18° C. to 30° C. and luminosity of 250 to 5000 lux. The antibiotics used in media for selection of transformed plant cells and tissues can be either kanamycin in the range of 25 mg/l to 200 mg/l, preferably 50 mg/l or hygromycin in the range of 5 mg/l to 100 mg/l, preferably 10 mg/l.

Further the said transformed plant cells and tissues is subcultured on medium containing a cytokinin preferably Zeatin in the range 0.01 to 5 mg/l, preferably 2 mg/l (($MS0Z_2H_{10}C$ medium) or a combination of cytokinins or combination of cytokinins in the range of 0.01 to 20 mg/l or combination of cytokinins and auxin, with the latter in the range of 0.01 to 5 mg/l, for further multiplication of shoot buds. The sub cultured shoot buds were transferred onto $MS0H_{10}C$ medium and allowed to grow to a length of 0.5 cm to 7 cm, preferably 1.5 cm.

Further the elongated shoot buds are transferred to a medium with low concentration of an auxin in the range of 0.01 to 2 mg/l for induction and growth of roots.

Another embodiment of the present invention is to provide methods for transforming *Abelmoschus* species, wherein the transformed shoot, plant cells and or tissues contain DNA/RNA sequences of interest, which is coding for genes or not wherein the said DNA/RNA sequences are transferred to subsequent generations by plant breeding techniques including but not limited to crosses. Further the invention provides for advancing the generation, wherein the said succeeding generations contain DNA/RNA sequences of interest with or with out the selectable marker gene (marker based or markerfree).

Another embodiment of the present invention is to provide a method for producing transformed plant, plant cells and tissues of *Abelmoschus esculentus* species wherein the said method comprising the steps of
a) surface sterilization of seeds and imbibing the seeds in water
b) germinating the seeds of step (a) in a suitable culture medium to obtain seedlings or explants
c) obtaining the explants from seedlings of step (a) or (b)
d) bombarding the explants of step (c) with tungsten or gold particles coated with DNA sequence of interest
e) culturing the explants of step (d) in a suitable culture medium to select the transformed plant cells and tissues
f) maintaining the transformed plant cells and tissues of step (e) in a suitable tissue culture medium to obtain shoot buds
g) culturing the shoot buds of step (f) in a suitable rooting medium for rooting to obtain transformed plants Further, the invention provides for regeneration of plants from *Abelmoschus* species wherein the species are selected from a group consisting of *A. caillei, A moschatus, A. manihot, A. tuberculatus, A. ficulneus, A. crinitus, A. angulosus A. tetraphyllus.*

Another embodiment of the present invention is to provide a method wherein the surface sterilized seeds are washed and imbibed in water for a period of 0 to 48 hours. Further, the surface sterilized seeds are placed on MS0 medium for germination (MS0 medium contains MS salts, B5 vitamins, 0.8% agar, 3% sucrose and pH 5.8).

Still another embodiment of the present invention is to provide a method for transforming *Abelmoschus* species, wherein the surface sterilized seeds are used to isolate the embryos in sterile conditions by pressing with tweezers or any other means and these embryos are washed in sterile water and blotted dry on filter paper and later placed on soaked sterile filter paper.

Another embodiment of the present invention is to provide a method for transforming *Abelmoschus* species, wherein the explants are selected from a group consisting of cotyledon with petiole, hypocotyls, embryo, immature embryo, leaf lamina, cotyledonary axil, shoot tip, anther, root and callus or other suitable explants.

Another embodiment of the present invention is to provide a method for transforming *Abelmoschus* species, wherein the embryos and various other explants are wounded with a sterile needle and further bombarding these explants with tungsten or gold particles coated with 1 to 10 μg of DNA sequence of interest wherein the bombardment pressure is in the range of 600 to 1500 psi (preferably 1100 psi).

Further the bombarded explants can be cultured on a various media known in prior art as medium containing a cytokinin, preferably Zeatin, in the range 0.01 to 5 mg/l, preferably 2 mg/l (($MS0Z_2H_{10}C$ medium) or a combination of cytokinins in the range of 0.01 to 20 mg/l or combination of cytokinins and auxin, with the latter in the range of 0.01 to 5 mg/l, containing antibiotic for selection of transformed plant cells and tissues. Further the said explant is incubated in plant tissue culture incubation room with temperature 18° C. to 30° C. and luminosity of 250 to 5000 lux. The antibiotics used in media for selection of transformed plant cells and tissues can be either kanamycin in the range of 25 mg/l to 200 mg/l, preferably 50 mg/l or hygromycin in the range of 5 mg/l to 100 mg/l, preferably 10 mg/l.

Further the said transformed plant cells and tissues is subcultured on medium containing a cytokinin preferably Zeatin in the range 0.01 to 5 mg/l, preferably 2 mg/l (($MS0Z_2H_{10}C$ medium) or a combination of cytokinins or combination of cytokinins in the range of 0.01 to 20 mg/l or combination of cytokinins and auxin, with the latter in the range of 0.01 to 5 mg/l, for further multiplication of shoot buds. The sub cultured shoot buds were transferred onto $MS0H_{10}C$ medium and allowed to grow to a length of 0.5 cm to 7 cm, preferably 1.5 cm.

Further the elongated shoot buds are transferred to a medium with low concentration of an auxin in the range of 0.01 to 2 mg/l for induction and growth of roots.

Another embodiment of the present invention is to provide a method for transforming *Abelmoschus* species wherein the said shoot, plant cells and/or tissues contain DNA/RNA sequences of interest which confers improved agronomic traits or combination of traits comprising for yield, drought resistance, stress resistance, nutritional value, inducing male sterility into the plant, cells and tissues or the transformed plant.

Another embodiment of the present invention is to provide a method for transforming *Abelmoschus* species wherein the said shoot, plant cells and/or tissues contain DNA/RNA sequences of interest which confers tolerance or resistance to disease, herbicide or insects to plant, cells and tissues wherein the said DNA/RNA sequences coding for genes or not.

Further the said DNA/RNA sequences are transferred to subsequent generations by plant breeding techniques including but not limited to crosses. Further the invention provides for advancing the generation, wherein the said succeeding generations contain DNA/RNA sequences of interest with or with out the selectable marker gene (marker based or markerfree).

Still another embodiment of the present invention is to provide transformed Okra Plant, plant cells and tissues which carry traits of agronomic and non-agronomic importance.

Still another embodiment of the present invention is to provide transformed plant, plant cells and tissues of *Abelmoschus* species using *Agrobacterium*-mediated or particle bombardment methods wherein the transformed okra plant carry the DNA/RNA sequence of interest wherein the transformed plant shows improved agronomic traits or a combination of traits comprising for yield, drought resistance, stress resistance, nutritional value, inducing male sterility into the plant, cells and tissues.

Still another embodiment of the present invention is to provide transformed plant, plant cells and tissues of *Abelmoschus* species using *Agrobacterium*-mediated or particle bombardment methods wherein the transformed okra plant carry the DNA/RNA sequence of interest wherein the transformed plant shows tolerance or resistance to disease, herbicide or insects.

6. A. Regeneration of *Abelmoschus* Species by Tissue Culture Method

Okra (*Abelmoschus esculentus*) genotypes representing a variety of agronomic varieties or hybrids [including Arka Anamika, Parbhani Kranti and proprietary lines of Maharashtra Hybrid Seeds Company Ltd. (MHSCL)] were used in these experiments. The seeds were surface sterilized preferably in 0.1% (weight/volume) $HgCl_2$ in distilled water for 2 to 60 minutes, preferably 30 minutes (commercially available other surface sterilizing agents also work instead of $HgCl_2$). These seeds were washed many times in sterile distilled water. The sterilized seeds were imbibed with water for a period of 0 to 48 hours. The seeds were germinated to obtain seedlings. Various explants were obtained from seeds and seedlings for regeneration of whole plants. The explants used for the present invention are selected from a group consisting of cotyledon with petiole, hypocotyls, embryo, immature embryo, leaf lamina, cotyledonary axil, shoot tip, anther, root and callus or other suitable explants. These explants were used for regeneration of the whole plant.

6. A. 1. Cotyledon with Petiole

The seeds mentioned in 6. A. were inoculated on MS0 medium (MS0 medium contains MS salts, B5 vitamins, 3% sucrose, 0.8% agar and adjusted the pH 5.8) in bottles and incubated under light for the germination of seeds in the tissue culture incubation room.

The explants viz., cotyledon with petiole were excised from seedlings (1 to 20 days old preferably 12 days old seedlings). These explants were inoculated on $MS0Z_2$ medium ($MS0Z_2$ medium contains MS salts, B5 vitamins, 3% sucrose, 0.8% agar, with a cytokinin preferably 2 mg/l Zeatin and adjusted the pH to 5.8) and incubated in the tissue culture incubation room.

Multiple shoot buds and calli were developed in more than 80% of the explants, from the cut ends of the petiole of cotyledon explants with petiole. Upon further transfer of the multiple shoot buds up to 5 fold multiplication was obtained. These shoot buds were separated and subcultured on MS0 medium for the further elongation of the shoots and induction of rooting. In 2 to 3 weeks these shoots elongated further and the roots become well developed. The rooted plants were hardened and established in green house. The procedures for hardening are similar to those in prior art.

All the tissue cultured plants grew normally till maturity. Seed setting was normal in all the plants.

The calli produced from cut ends of the petiole and lamina of cotyledons were subcultured at an interval of 2 to 4 weeks (preferably 3 weeks) on $MS0Z_2$ medium. By the end of this period these calli developed to a larger size.

6. A. 2. Hypocotyls

The seeds mentioned in 4. A. were inoculated on MS0 medium in bottles and incubated under light for the germination of seeds. The hypocotyl explants were excised from 5 to 20 days old seedlings (preferably 12 days old seedlings). These explants were inoculated on MS0Z2 medium.

Multiple shoot buds and callus were developed in 75+% of the explants, from the cut ends of hypocotyl explants in 2 to 6 weeks period. Upon further transfer of the multiple shoot buds up to 5 fold multiplication was obtained. These shoot buds were separated and subcultured on MS0 medium for further elongation of the shoots and rooting. In 2 to 4 weeks these shoots were further elongated and the roots were well developed. The rooted plants were hardened and established in green house.

All the tissue cultured plants grew normally till maturity. Seed setting was normal in all the plants.

The calli produced from cut ends of the hypocotyls were subcultured at an interval of 2 to 4 weeks preferably 3 weeks interval on $MS0Z_2$ medium. On subculture these calli were grown in size.

6. A. 3. Mature Embryo

The seeds mentioned in 6. A. were used in these experiments; preferably these seeds were imbibed in sterile water. The embryos were isolated from these seeds in sterile conditions by pressing to remove the seed coat with tweezers or any other means. The imbibed seeds are preferred over non-imbibed (However the positive responses were obtained from imbibed and non-imbibed seeds). The cotyledons were separated from embryos and these embryos measure 1 to 8 mm (preferably 5 mm) long at the time of isolation. These isolated embryos were washed in sterile water and blot dried. These embryos were wounded at the plumule tip.

These embryos were transferred on MS0Z2 medium for 2 to 4 weeks preferably for 3 weeks period. Multiple shoot bud clumps were developed and subcultured at 2 to 4 weeks interval preferably at 3 weeks interval on MS0 medium. The frequency of shoot bud induction from the explants was greater than 90% on MS0Z2 medium. Upon further transfer of the multiple shoot buds up to 5 fold multiplication was obtained. Shoots (preferably 1.5 cm) were transferred on MS0 medium in bottles for further elongation and rooting. After 1 to 5 weeks in the rooting medium the shoots were further elongated and the roots were well developed.

These (R0) regenerated plants were hardened and established in green house. All the tissue cultured plants grew normally till maturity. Seed setting was normal in all the plants.

6. B. Okra Transformations for Transgene Expression
Preparation of Explants for Transformation 6. B. 1. Cotyledon with Petiole
Preparation of cotyledon explants is mentioned in 6. A. 1.

6. B. 2. Hypocotyl
Preparation of hypocotyl explants is mentioned in 6. A. 2.

6. B. 3. Mature Embryo
Preparation of mature embryo explants is mentioned in 6. A. 3.

6. B. 4. Immature Embryo
Green fruits were collected (2 cm to 12 cm) and surface sterilized in 0.1% (weight/volume) $HgCl_2$ in distilled water (for 1 to 60 minutes preferably for 5 minutes) and further washed in sterile distilled water.

Immature embryos were isolated from these fruits in sterile conditions (preferably by using tweezers or any other means) and used for transformation.

6. B. 5. Leaf Lamina

Leaf lamina were isolated from Okra plants (preferably from in vitro grown) and used for transformation.

6. B. 6. Cotyledonary Axil

The seeds were surface sterilized preferably in 0.1% (weight/volume) $HgCl_2$ in distilled water (for 1 to 60 minutes, preferably 30 minutes). These seeds were washed many times in sterile distilled water and inoculated on a medium (preferably on MS0 medium in bottles) and incubated under light for the germination of seeds. The explants viz., cotyledon axils were excised from seedlings (5 to 20 days, preferably 12 days old seedlings) and used for transformation.

6. B. 7. Shoot Tip

The seeds were surface sterilized preferably in 0.1% (weight/volume) $HgCl_2$ in distilled water (for 1 to 60 minutes, preferably 30 minutes). These seeds were washed many times in sterile distilled water and inoculated on MS0 medium in bottles and incubated under light for the germination of seeds. The explants viz., shoot tips were excised from seedlings (preferably 12 days old seedlings) and used for transformation.

6. B. 8. Anther

Anthers were isolated in sterile conditions from unopened flower buds or flowers were used for the transformations.

6. B. 9. Root

The roots were excised from plants (preferably grown in vitro) and were used for transformation.

6. B. 10. Callus

The calli grown in vitro, were used for transformations. These explants, as mentioned in above sections 6. B. 1 to 6. B. 10, were used for *Agrobacterium*-mediated method or Biolistic method of transformation. The transformed plant cells or tissues or plant were analyzed for the transient/or stable GUS assay. The transformed plants were further analyzed using standard molecular tools well known in prior art such as Southern blotting, copy number estimation, and western blotting.

6. C. *Agrobacterium*-Mediated Method of Transformation

The vector pC 1301 contains the GUS and hpt genes linked to 35S promoter from Cauliflower Mosaic Virus (CaMV 35 S) and introduced into *Agrobacterium tumefaciens* strain LBA 4404 to produce recombinant strain.

Recombinant *A. tumefaciens* (LBA 4404 pC 1301) strain was inoculated into a suitable medium for the growth of *Agrobacterium*. Usually *Agrobacterium* was inoculated into 25 ml of sterile 2YT medium (pH 7) in a flask. 2YT medium contains 1% Yeast extract, 1.6% Tryptone and 0.5% NaCl. The antibiotics 10 mg/l Rifampicin, 20 mg/l Streptomycin, and 75 mg/l Kanamycin were added before inoculating bacteria for the selective growth of recombinant *Agrobacterium* with the plasmid 1301. Different plasmids containing DNA/RNA sequence of interest were also used for producing recombinant *Agrobacterium* strains for Example plasmid pC 1201 can also be used for producing recombinant *Agrobacterium* strains Yeast extract, Tryptone and NaCl were purchased from HiMedia Labs, Mumbai, India. The bacteria were inoculated in 2YT medium in flask and kept on a shaker to get Optical Density (600 nm) of 0.01 to 2.5 preferably 1.8.

6. D. Inoculation of Explants with Recombinant *Agrobacterium tumefaciens*

The above prepared explants (described in 6. B. 1 to 6 B. 10) were inoculated in *Agrobacterium* suspension (preferably 15 minutes), blotted dry on sterile filter paper and later transferred to Petri dishes (preferably 20 embryos per Petri dish) on MS0 As medium [MS0 As medium contains MS salts (Murashige and Skoog. Physiol. Plant. (1962) 15:473-497, B5 vitamins (Gamborg et al., Exp. Cell Res. (1968) 50:151-158) 0.8% agar, 3% sucrose and pH 5.8 (Preferably enriched with 3,5-Dimethoxy-4-hydroxyaceto-phenone, preferably in the concentration of 100 mM).

These petri dishes were incubated in tissue culture incubation room. After the co-cultivation period (2 to 5 days, preferably 2 days) these explants were assayed for transient GUS expression or transferred onto $MS0Z_2H_{10}C$ medium $MS0Z_2H_{10}C$ contains MS salts, B5 vitamins, 3% sucrose, 0.8% agar, pH 5.8, cytokinin preferably Zeatin in the range 0.05 to 5 mg/l, (preferably 2 mg/l Zeatin) supplemented with 5 mg/l to 100 mg/l Hygromycin B (preferably 10 mg/l Hygromycin B) and taken for the stable GUS assay.

GUS activity was detected by the histochemical assay using 5-bromo-4-chloro-3-indolyl-β-D-glucoronide as substrate (Jefferson et al., Proc. Natl. Acad. Sci. USA (1986) 83:8447-8451) and were incubated in 100 mM phosphate buffer (pH 7.0) containing 1 mg/ml X-gluc for overnight at 37° C. temperature.

X-gluc was purchased from Duchefa, Haarlem, The Netherlands.

All the type of explants showed GUS expression. The results of these GUS assay are tabulated in 6. F as Table 1. The various explants showing GUS expression are shown in the following figures. The mature embryo having GUS expression is shown in FIG. 1A. The cotyledonary axil having GUS expression is shown in FIG. 1B. The shoot tip having GUS expression is shown in FIG. 1C. The transformed callus having GUS expression is shown in FIG. 1D.

6. E. Microprojectile/Particle Bombardment-Method of Transformation

A number of plasmids were used in these experiments including plasmid pC 1301 and plasmid 'pC 1201' for transformation.

All experiments were conducted with the Biolistic PDS-1000/He system (Sanford, TIB (1988) 6:299-302. Sanford et al., Technique J. Methods Cell Mol. Biol. (1991) 3:3-16) using tungsten or gold particles (3 mg) in the diameter of 0.1 to 3 μm. These particles were previously washed in ethanol were in aqueous suspension (50 μl) were coated with 5 to 10 μg of plasmid DNA. The procedure followed for the coating of DNA on gold was as described by Kikkert et al., Plant Cell Tissue and Organ Culture (1993) 33:221-226.

The particles were finely dispersed with an ultra sonicator (Elma Transonic 460 Lab-Line Instruments Inc., IL, USA) before bombardment.

The explants were arranged in the center of the petri plate on a tissue culture medium. Bombardment pressure in the range of 900 to 1500 PSI (preferably 1100 PSI) was used. The distance from the launching plate was in the range of 6 to 18 cm, (preferably 6 cm) were used. (The gold and tungsten particles were purchased from Bio-Rad Labs., 2000 Alfred Nobel Drive, Hercules, Calif. 94547 USA).

After bombardment of the explants as mentioned in section 6 E, these were placed on MS0 medium for 2 to 5 days (preferably 3 days). After 2 to 5 days (preferably 3 days) these embryos were used for transient GUS assay or transferred on $MS0Z_2H_{10}$ medium [$MS0Z_2H_{10}C$ contains MS salts, B5 vitamins, 3% sucrose, 0.8% agar, pH 5.8, cytokinin preferably Zeatin in the range 0.05 to 5 mg/l, (preferably 2 mg/l Zeatin) supplemented with 5 mg/l to 100 mg/l Hygromycin B (preferably 10 mg/l Hygromycin B) and taken for the stable GUS assay.

GUS activity was detected by the histo chemical assay using 5-bromo-4-chloro-3-indolyl-β-D-glucoronide as substrate (Jefferson et al., Proc. Natl. Acad. Sci. USA (1986)

83:8447-8451) and were incubated in 100 mM phosphate buffer (pH 7.0) containing 1 mg/ml X-gluc for overnight at 37° C. temperature.

All the types of explants showed GUS expression. Various explants showing GUS expression are shown in the following figures. The transformed mature embryo showing GUS activity is shown in FIG. 2A. The transformed callus showing GUS activity is shown in FIG. 2B and the transformed anther showing GUS activity is shown in FIG. 2C.

The results of these GUS assay are tabulated in Table 1 and in section below.

6. F. Results of Transient Gus Expression Using Different Okra Explants

Various explants were used for transformation using both *Agrobacterium*-mediated transformation and Biolistic-methods. The explants were screened using GUS assay. The data from this assay are tabulated in Table 1.

TABLE 1

| Sr. No. | Explant | *Agrobacterium* - mediated transformation # of GUS explants positive/# of explants assayed | Biolistic - mediated transformation # of GUS explants positive/# of explants assayed |
|---|---|---|---|
| 1 | Cotyledon with petiole | 35/40 | 34/40 |
| 2 | Hypocotyl | 30/35 | 31/38 |
| 3 | Mature embryo | 38/38 | 42/42 |
| 4 | Immature embryo | 36/37 | 24/40 |
| 5 | Leaf lamina | 37/37 | 17/40 |
| 6 | Cotyledonary axil | 21/30 | 14/40 |
| 7 | Shoot tip | 25/30 | 16/29 |
| 8 | Anther | 22/40 | 12/30 |
| 9 | Root | 09/40 | 12/40 |
| 10 | Callus | 09/40 | 08/40 |

The above mentioned explant types were also positive in stable GUS expression in GUS assays when tested after 1 month. It is clear from these experiments that all explants used are amenable to transformation. However it is evident that mature embryo is the most efficient explant to use for transformation either by *Agrobacterium*-mediated or Biolistic-method. The various explant types were carried forward for the generation of the transgenic plants. The transformed plants were also analyzed using standard molecular methodology known in the prior art. These plants were advanced to subsequent generations and analyzed for the presence of heterologous genes integrated in genome. These are illustrated in the following examples.

The following examples are for understanding the invention and should not be construed as to limit the scope of the invention.

EXAMPLES

Example 1

*Agrobacterium*-Mediated Transformation of Okra Embryos Using GUS and hpt Genes (Marker Based/Linked System, Co-Cultivation on MS0 Medium)

A. Preparation of Plant Material

Okra genotypes representing a variety of agronomic varieties or hybrids [including Arka Anamika, Parbhani Kranti and proprietary lines of Maharashtra Hybrid Seeds Company Ltd. (MHSCL)] were used in these experiments.

The seeds were surface sterilized preferably in 0.1% (weight/volume) $HgCl_2$ in distilled water (for 1 to 60 minutes, preferably 30 minutes). These mature seeds were washed many times in sterile distilled water. The surface sterilized seeds were imbibed in sterile water for a period of 0 to 48 hours preferably for 16 hrs.

The embryos were isolated from these seeds in sterile conditions by pressing to remove the seed coat with tweezers or any other means. The cotyledons were separated from embryos, and these embryos measure 1 to 8 mm (preferably 5 mm) long at the time of isolation. These isolated embryos were washed many times in sterile water blotted dry on filter paper. These embryos were wounded at the plumule tip.

B. Preparation of Transgenic *Agrobacterium tumefaciens*:

The vector pC 1301 contains the GUS and hpt genes linked to 35S promoter from Cauliflower Mosaic Virus (CaMV 35S) and introduced into *Agrobacterium tumefaciens* strain LBA4404.

*A. tumefaciens* (LBA 4404 pC 1301) was inoculated into a suitable medium for the growth of *Agrobacterium*. Usually *Agrobacterium* was inoculated into 25 ml of sterile 2YT medium (pH 7) in a flask. 2YT medium contains 1% Yeast extract, 1.6% Tryptone and 0.5% NaCl. The antibiotics 10 mg/l Rifampicin, 20 mg/l Streptomycin, and 75 mg/l Kanamycin were added before inoculating bacteria for the selective growth of *Agrobacterium* with the plasmid 1301.

Yeast extract, Tryptone and NaCl were purchased from HiMedia Labs, Mumbai, India. The bacteria were inoculated in 2YT medium in flask and kept on a shaker to get Optical Density (600 nm) of 0.01 to 2.5, preferably 1.8.

C. Inoculation of Explants with Recombinant *Agrobacterium tumefaciens*

These wounded embryos were inoculated in *Agrobacterium* suspension (preferably 15 minutes), blotted dry on sterile filter paper and later transferred to Petri dishes (preferably 20 embryos per petri dish) on MS0 medium [MS0 medium contains MS salts (Murashige and Skoog., Physiol. Plant. (1962) 15:473-497, B5 vitamins (Gamborg et al., Exp. Cell Res. (1968) 50:151-158) 0.8% agar, 3% sucrose and pH 5.8.

D. Regeneration of Transformed Plants After Co-Cultivation

The petri dishes containing wounded embryos were incubated in tissue culture incubation room. After co-cultivation period (2 to 5 days preferably 2 days of co-cultivation) these explants were washed in liquid MS0 medium (liquid MS0 medium contains MS salts, B5 vitamins, 3% sucrose and pH 5.8) with 500 mg/l Cefotaxime to kill the *Agrobacterium* and transferred on $MS0Z_2H_{10}C$ medium [$MS0Z_2H_{10}C$ contains MS salts, B5 vitamins, 3% sucrose, 0.8% agar, pH 5.8, cytokinin/s preferably Zeatin in the range 0.05 to 5 mg/l, (preferably 2 mg/l Zeatin) supplemented with 5 mg/l to 100 mg/l Hygromycin B (preferably 10 mg/l Hygromycin B) were incubated per petri dish and were transferred onto fresh medium after a period of 2 to 5 weeks (preferably 3 weeks).

Between $4^{th}$ and $7^{th}$ weeks on $MS0Z_2H_{10}C$ medium, multiple shoot buds developed from the plumule of the embryo (FIG. 8).

These multiple shoot buds were subcultured on $MS0H_{10}C$ ($MS0H_{10}C$ contains MS salts, B5 vitamins, 3% sucrose, 0.8% agar and adjusted the pH 5.8 supplemented with 10 mg/l Hygromycin B and 500 mg/l Cefotaxime) medium at the interval of 2 to 4 weeks. These shoot bud clumps are shown in FIG. 8 were separated by cutting and subcultured on same media for 3 weeks to develop shoots (preferably shoots of the size 1.5 cm). The said shoots were transferred onto $MS0H_{10}C$ medium in bottles for further elongation and rooting. After 1 to 5 weeks in the rooting medium, the shoots were elongated further and the roots were well developed (FIG. 3B).

The rooted plants were hardened and established in green house (FIG. 3C). All these plants grew normally till maturity. Seed setting was normal in all the plants.

A total of 180 embryos were inoculated in *Agrobacterium* in this experiment. Rooted plants were tested by GUS assay. A total of 6 plants were positive for GUS expression.

Zeatin and agar were purchased from HiMedia Labs, Mumbai, India. Hygromycin B was purchased from A.G. Scientific, Inc. 6450 Lusk Blvd, San Diego, USA. 3,5-Dimethoxy-4-hydroxyaceto-phenone was purchased from Sigma-Aldrich Chemie Gmbh, Riedstr. Steinheim, Germany.

Sucrose was purchased from Sisco Research Lab. Pvt. Ltd., Mumbai, India.

E. Assay for Gus Expression

GUS activity was detected by the histochemical assay using 5-bromo-4-chloro-3-indolyl-β-D-glucoronide as substrate (Jefferson et al., Proc. Natl. Acad. Sci. USA (1986) 83:8447-8451) and were incubated in 100 mM phosphate buffer (pH 7.0) containing 1 mg/ml X-gluc for overnight at 37° C. temperature.

Figure 4:

These 6 primary transformants ($T_0$ generation plants) were established in green house and were selfed and the $T_1$ generation seeds were collected. Two days old $T_1$ generation seedlings were used for GUS assay. The GUS expression was found in the $T_1$ seedlings tested as shown in FIG. 4. The segregation pattern for GUS activity in these progenies indicates that the integration of GUS gene appears to be confined to a single locus in the genome (Table No. 2).

Transgenic $T_1$ generation okra seedlings are positive for GUS expression

TABLE NO. 2

Segregation analysis of GUS gene expression in $T_1$ generation seedlings.

| Plant ID | Number of $T_1$ seedlings tested by GUS assay | Number of seedlings positive for GUS expression | Number of seedlings negative for GUS expression | Chi$^2$ value for the segregation of GUS gene | Segregation ratio (Transgenic: Non transgenic) |
|---|---|---|---|---|---|
| TOG3 | 24 | 20 | 4 | 0.88 | 3:1 |

To rule out the possibility of GUS expression in non-transgenic plants, samples from these control plants were also assayed. The GUS expression was not found in these non-transgenic control plants. This result confirms that plants showing GUS activity are transgenic as shown in FIG. 4.

These plants were selfed and further the $R_1$ generation seeds were collected. $R_1$ generation seedlings were raised from these seeds. The leaf samples from these non transgenic plants were used as controls for the GUS assay.

The GUS activity was not found in the non transgenic seedlings as expected.

F. Negative Control for Transformation

Negative controls were maintained in each experiment to ensure that the hygromycin killed the growth of non-transgenic tissue. After the isolation, these embryos were wounded as mentioned above and without inoculating in bacteria, embryos were incubated for 2 days at the rate of 10 embryos per plate on MS0 As medium. After 2 days, these embryos were transferred on MS0Z$_2$H$_{10}$C for 2 to 4 weeks' period. All these embryos completely bleached on selection medium by the end of 5$^{th}$ subculture. This indicates that Hygromycin concentration (5-100 mg/l, preferably 10 mg/l) was sufficient to control the non-transgenic growth of tissue in these experiments.

Example No. 2

*Agrobacterium*-Mediated Transformation of Okra Embryos Using GUS and hpt Genes (Marker Based System, Co-Cultivation on MS0Z$_2$As Medium)

A. Preparation of Plant Material

Okra genotypes representing a variety of agronomic varieties or hybrids [including Arka Anamika, Parbhani Kranti and proprietary lines of Maharashtra Hybrid Seeds Company Ltd. (MHSCL)] were used in these experiments.

The seeds were surface sterilized preferably in 0.1% (weight/volume) HgCl$_2$ in distilled water for 1 to 60 minutes (preferably 30 minutes). These seeds were washed many times in sterile distilled water and preferably imbibed in sterile water.

The embryos were isolated from these seeds in sterile conditions by pressing to remove the seed coat with tweezers or any other means. The imbibed seeds were preferred over non-imbibed. The cotyledons were separated from embryos, and these embryos measure 1 to 8 mm long (preferably 5 mm long) at the time of isolation. These isolated embryos were washed many times in sterile water blotted dry on filter paper and placed on soaked sterile filter paper. These embryos were wounded at the plumule tip.

B. Preparation of Transgenic *Agrobacterium tumefaciens*:

The vector pC 1301 contains the GUS and hpt genes linked to 35S promoter from Cauliflower Mosaic Virus (CaMV 35S) and introduced into *Agrobacterium tumefaciens* strain LBA4404.

The recombinant *A. tumefaciens* (LBA 4404 pC 1301) was inoculated into a suitable medium for the growth of *Agrobacterium*. Usually *Agrobacterium* was inoculated into 25 ml of sterile 2YT medium (pH 7) in a flask. 2YT medium contains 1% Yeast extract, 1.6% Tryptone and 0.5% NaCl. The antibiotics 10 mg/l Rifampicin, 20 mg/l Streptomycin, and 75 mg/l Kanamycin were added before inoculating bacteria for the selective growth of *Agrobacterium* with the plasmid 1301.

Yeast extract, Tryptone and NaCl were purchased from HiMedia Labs, Mumbai, India. The bacteria were inoculated in 2YT medium in flask and kept on a shaker to get Optical Density (600 nm) in the range of 0.01 to 2, preferably 1.8.

C. Inoculation of Explants with Transgenic *Agrobacterium tumefaciens*

These wounded embryos were inoculated in recombinant *Agrobacterium* suspension (preferably 15 minutes), blotted dry on sterile filter paper and later transferred to Petri dishes on MS0Z$_2$As medium (MS0Z$_2$As contains 0.05 to 5 mg/l Zeatin, preferably 2 mg/l Zeatin, MS salts (Murashige and Skoog., Physiol. Plant. (1962) 15:473-497), B5 vitamins (Gamborg et al., Exp. Cell Res. (1968) 50:151-158) 0.8% agar, 3% sucrose and pH 5.8 enriched with preferably 100 mM 3,5-Dimethoxy-4-hydroxyaceto-phenone).

After the co-cultivation (2 to 5 days preferably 2 days of co-cultivation), these explants were washed in liquid MS0 medium (liquid MS0 medium contains MS salts, B5 vitamins, 3% sucrose and pH 5.8) with 500 mg/l Cefotaxime to kill the *Agrobacterium* and were transferred on MS0Z2H10C medium (MS0Z2H10C contains MS salts, B5 vitamins, 3% sucrose, 0.8% agar, pH 5.8, 0.05 to 5 mg/l Zeatin (preferably 2 mg/l Zeatin) supplemented with 5 mg/l to 100 mg/l Hygromycin B (preferably 10 mg/l Hygromycin B) and preferably 500 mg/l Cefotaxime (any other antibiotic) to kill the *Agrobacterium*. About 5 to 20 developing embryos (preferably 10 embryos) were incubated per petri dish and were transferred onto fresh medium after a period of 2 to 5 weeks (preferably 3 weeks).

By the end of 4th to 7th weeks, preferably 6th week on MS0Z2H10C medium, multiple shoot buds developed from the plumule tip of the embryo.

These multiple shoot buds were subcultured on MS0H10C (MS0H10C contains MS salts, B5 vitamins, 3% sucrose, 0.8% agar and adjusted the pH 5.8 supplemented with 10 mg/l Hygromycin B and 500 mg/l Cefotaxime) medium at the interval of 3 weeks. These shoot bud clumps were separated by cutting and subcultured on same media for 2 to 5 weeks to develop shoots (preferably about 1.5 cm in size). The said shoots were transferred onto MS0H10C medium in bottles for further elongation and rooting. After 2 to 4 weeks in the rooting medium, the shoots were elongated further and the roots were well developed.

The rooted plants were hardened and established in green house. A total of 300 embryos were inoculated in *Agrobacterium* in this experiment. Rooted plants were tested by GUS assay. A total of 6 plants were positive for GUS expression. All these 6 plants grew normally till maturity. Seed setting was normal in all the plants. Experiments were conducted several times to obtain transformed plants with similar results.

GUS activity was detected by the histochemical assay using 5-bromo-4-chloro-3-indolyl-β-D-glucoronide as substrate (Jefferson et al., Proc. Natl. Acad. Sci. USA (1986) 83:8447-8451). Plant segments or leaf segments were incubated in 100 mM phosphate buffer (pH 7.0) containing 1 mg/ml X-gluc overnight at about 370 C. temperature.

Zeatin and agar were purchased from HiMedia Labs, Mumbai, India

Hygromycin B was purchased from A.G. Scientific, Inc. 6450 Lusk Blvd, San Diego, USA.

3,5-Dimethoxy-4-hydroxyaceto-phenone was purchased from Sigma-Aldrich Chemie Gmbh, Riedstr. Steinheim, Germany.

D. Assay for Gus Expression

The leaves cut from rooted plants were taken for GUS assay. In this experiment 6 plants were positive for GUS expression.

To rule out the possibility of GUS expression in non-transgenic plants, samples from these control plants were also assayed. The GUS expression was not found in these non-transgenic control plants as expected. This result confirms that plants expressing GUS gene were transgenic.

These primary transformants ($T_0$ generation plants) were established in green house and were selfed and the $T_1$ generation seeds were collected. These plants were advanced to further generations.

E. Negative Control for Transformation

Negative controls were maintained in each experiment to ensure that the hygromycin killed the growth of non-transgenic tissue. A total of 20 embryos were maintained as negative control. After the isolation, these embryos were wounded as mentioned above and without inoculating in bacteria, embryos were incubated for 2 days at the rate of 5 to 20, preferably 10 embryos per plate on MS0Z$_2$As medium. After 2 days, these embryos were transferred on MS0Z$_2$H$_{10}$C for 2 to 5 weeks period. Out of 20 embryos, 10 produced multiple shoot buds which were sub-cultured at 3 weeks interval on MS0Z$_2$H$_{10}$C. But these multiple shoot buds were completely bleached by the end of $5^{th}$ subculture. This proves Hygromycin concentration (5 to 100 mg/l, preferably 10 mg/l) was sufficient to control the non-transgenic growth of tissue in these experiments.

Example No. 3

*Agrobacterium*-Mediated Transformation of Okra Embryos Using Cry1A(c)/Cry2Ab etc. and NPT II Genes for the Generation of Insect Resistance Transgenic Okra (Marker Based System, Cocultivation on MS0 As Medium)

A. Preparation of Explants:

Okra genotypes representing a variety of agronomic varieties or hybrids [including Arka Anamika, Parbhani Kranti and proprietary lines of Maharashtra Hybrid Seeds Company Ltd. (MHSCL)] were used in these experiments.

The mature seeds were surface sterilized preferably in 0.1% (weight/volume) $HgCl_2$ in distilled water for 1 to 60 minutes (preferably 30 minutes). These seeds were washed many times in sterile distilled water (Preferably, these seeds were imbibed in sterile water).

The embryos were isolated from these seeds in sterile conditions by pressing to remove the seed coat with tweezers or any other means. The imbibed seeds were preferred over non-imbibed. However the non-imbibed seeds also can be used. The cotyledons were separated from embryos, and these embryos measure 1 to 8 mm preferably 5 mm long at the time of isolation. These isolated embryos were washed many times in sterile water blotted dry on filter paper and placed on soaked sterile filter paper. These embryos were wounded at the plumule tip and used for the co-cultivation in *Agrobacterium* suspension.

B. Preparation of Recombinant *Agrobacterium tumefaciens*

The vectors used were pC 2300 which carries Cry2Ab/Cry1A(c) gene and nptII gene as plant selectable marker in the T-DNA of this plasmid. One of these plasmids was introduced into the *Agrobacterium tumefaciens* strain EHA 105 and used for the transformations.

The recombinant *Agrobacterium* strain carrying Bt gene (Cry2Ab or Cry1A(c) etc.) in the plasmid pC 2300 was used for transformation of okra plants.

The antibiotic 50 mg/l kanamycin and 10 mg/l chloramphenicol were added to 2YT medium for the selective growth of the *Agrobacterium* with the plasmid containing either Cry1A(c) or Cry2Ab gene.

The antibiotic kanamycin (preferably 50 mg/l) was used to select the transgenic tissue on MS0Z$_2$K$_{50}$C medium (MS0Z$_2$K$_{50}$C medium contains MS salts, B5 vitamins, 3% sucrose, 0.8% agar, pH 5.8, 2 mg/l Zeatin supplemented with 25 to 200 mg/l, preferably 50 mg/l kanamycin and preferably 500 mg/l Cefotaxime or any other antibiotic to kill the *Agrobacterium*).

Kanamycin was purchased from Macleods Pharma., Daman, U. T., India.

C. Analysis of Putative Transgenic Plants Using Double Antibody Sandwich ELISA.

The putative transformed plants were tested for the expression of the Bt genes, Cry1A(c) or Cry2Ab, using ELISA assay.

The ELISA plate was coated with monoclonal antibodies specific to Cry1A(c) or Cry2Ab protein and these plates were supplied from Desigen Diagnostics, Division of MAHYCO seeds Ltd., Maharashtra, India. According to the manufacturer's protocol the assay was carried out as follows. 2 to 4 leaf discs of the diameter 1 cm were taken from putative transgenic plants and control plants. These leaf samples were extracted in 500 µl of 1×PBST buffer. 50 µl of sample was loaded to each well in the pre-coated plate. After sample loading 150 µl of polyclonal antibodies specific to Cry1A(c) or Cry2Ab in the ratio 1:20,000 dilution in PBSTO was added to each well. This plate was stored at 4° C. overnight. The overnight incubated plate was washed thrice with PBST on the next day. 200 µl per well detection antibody labeled with alkaline phosphate at 1:6000 dilution in PBSTO, was added to these washed plates. This plate was incubated for 2 hours at room temperature. After the incubation this plate was washed thrice with PBST. Finally 250 µI substrate buffer containing 1 mg/ml paranitro phenyl phosphate was added per well and the color development was recorded at 405 nm wavelength using an ELISA reader. The positive samples were selected on the development of yellow color giving OD value>0.2 (after 30 minutes incubation) after subtracting the blank value which was compared to the negative (non-transgenic) control. Composition of all the buffers used for ELISA is summarized in Table 3.

TABLE NO. 3

Details for the buffers used for ELISA for screening putative transgenic plants

| Buffer | Components for 1 liter | Make |
| --- | --- | --- |
| 10X PBST (pH 7.4) | 10X PBST buffer was prepared by adding 80 gm/l Sodium chloride, 11.5 gm/l Sodium phosphate dibasic, 2 gm/l potassium chloride and 2 gm/l Potassium dihydrogen phosphate and adjusted the pH to 7.4. After making up the volume to 1 liter, 5 ml of Tween 20 was added. | Sodium chloride was purchased from Merck (India) Limited, Worli, Bombay, India. Sodium phosphate dibasic was purchased from Sisco Research Lab. Mumbai, India. Potassium chloride, Potassium dihydrogen phosphate were purchased from HiMedia Labs, Mumbai, India. |
| 1X PBST | 1X PBST buffer was prepared by diluting 10X PBST buffer using distilled water | |
| 1X PBSTO | 1X PBST with 0.5% Ovalbumin | Ovalbumin was purchased from HiMedia Labs, Mumbai, India. |
| Substrate buffer | Ethanolamine = 96 ml HCl + Milli Q water = 52 ml + 48 ml = 100 ml Made up the final volume to 1 liter by adding Milli Q water | Ethanolamine was purchased from SD fine Chem. Boisar, India. |

ELISA results of 25 transgenic Okra plants positive for Bt with the respective ELISA readings.

TABLE NO. 4

| Sr. No. | Plant ID | ELISA reading |
| --- | --- | --- |
| 1 | TOC2b | 0.64 |
| 2 | TOC3a | 0.74 |
| 3 | TOC4a | 0.26 |
| 4 | TOC5 | 0.41 |
| 5 | TOC9a | 0.64 |
| 6 | TOC12 | 0.66 |
| 7 | TOC13 | 0.36 |

TABLE NO. 4-continued

| Sr. No. | Plant ID | ELISA reading |
| --- | --- | --- |
| 8 | TOC29b | 0.45 |
| 9 | TOC32a | 0.58 |
| 10 | TOC41a | 0.68 |
| 11 | TOC42a | 0.58 |
| 12 | TOC43a | 0.79 |
| 13 | TOC44a | 0.81 |
| 14 | TOC45 | 0.64 |
| 15 | TOC46a | 0.6 |
| 16 | TOC49a | 0.63 |
| 17 | TOC50a | 0.62 |
| 18 | TOC52a | 0.75 |
| 19 | TOC53 | 0.78 |
| 20 | TOC54 | 0.7 |
| 21 | TOC55a | 0.57 |
| 22 | TOC58 | 0.64 |
| 23 | TOC59 | 0.32 |
| 24 | TOC60a | 0.44 |
| 25 | TOC62a | 0.49 |
| Okra (Non transgenic) | NTO1 | 0.01 |

D. Insect Bioassays Using Transgenic and Nontransgenic Fruits

The larvae (second instar) of these insects pests viz., Shoot and fruit borer (*Earias vitella, E. insulana*) and the Fruit borer (*Helicoverpa armigera*) were reared in the laboratory, were released separately on the young fruits from these transgenic plants. The fruits were placed in glass bottle and covered with cloth for aeration. Larval mortality if any was recorded after 3 days. On transgenic fruits all the larvae of these insects were dead where as on non transgenic they were alive and healthy. These results indicate very high resistance to the target pests in the transgenic plants (Data of bioassay is summarized in Table No. 5).

TABLE NO. 5

Results of insect bioassays using Okra fruit samples

| Plant type | Name of insect larvae used | Number of larvae/fruit | Status of larvae after 3 days |
| --- | --- | --- | --- |
| Transgnic Bt Okra | *Helicoverpa armigera* | 5 | Dead |
| Non transgenic control Okra | *Helicoverpa armigera* | 5 | Live |
| Transgnic Bt Okra | *Earias vitella* | 5 | Dead |
| Non transgenic control Okra | *Earias vitella* | 5 | Live |

Fruits from non transgenic plants were used in the insect bioassays as mentioned above in Table No. 5. The fruits of these plants were susceptible for the insect pests damage.

Mendelian segregation ratio of 3:1, for presence the of Bt protein: absence of Bt protein, was observed in the progenies of a large number of transgenic lines, whereas few lines did not segregate in 3:1 ratio. The segregation results of 4 transgenic lines are tabulated in the Table No. 6.

TABLE NO. 6

Segregation analysis of Bt gene in transgenic Okra $T_1$ generation seedlings from four events.

| Sr. No. | Plant ID | Number of $T_1$ seedlings tested by ELISA | Number of seedlings positive for Bt in ELISA | Number of seedlings negative for Bt in ELISA | $Chi^2$ value for the segregation of Bt gene | Segregation ratio (Bt:Non Bt) |
|---|---|---|---|---|---|---|
| 1 | TOC14a | 28 | 12 | 16 | 15.42 | 3:4 |
| 2 | TOC17a | 26 | 16 | 10 | 2.52 | 3:1 |
| 3 | TOC24A | 17 | 11 | 6 | 0.96 | 3:1 |
| 4 | TOC38 | 17 | 13 | 4 | 0.02 | 3:1 |

E. Tissue Culture Controls

The non transgenic (tissue cultured) control plants were selfed and the R1 generation seeds were collected. R1 generation seedlings were raised from these seeds. The leaf samples from these non transgenic plants were used as controls for the ELISA. The Bt protein activity was not found in the non transgenic seedlings as expected.

F. Negative Control for Transformation

Negative controls were maintained in each experiment to ensure that the kanamycin killed the growth of non-transgenic tissue. After the isolation, these embryos were wounded as mentioned above and without inoculating in bacteria, these embryos were incubated for 2 days at the rate of 10 embryos per plate on MS0 As medium. After 2 days, these embryos were transferred on $MS0Z_2K_{50}C$ for a period of 3 weeks onto $MS0Z_2K_{50}C$ medium.

These explants bleached on $1^{st}$ selection in the period of 3 weeks. This proves kanamycin concentration (preferably 50 mg/l) was sufficient to kill the non-transgenic tissue in these experiments.

Example No. 4

Agrobacterium (EHA 105 Strain)-Mediated Transformation of Okra Embryos Using Cry1A(c) and NPT II Genes for the Generation of Insect Resistant Transgenic Okra [Marker Based System, Cocultivation on MS0 Medium]

A. Preparation of Plant Material

Okra genotypes representing a variety of agronomic varieties or hybrids [including Arka Anamika, Parbhani Kranti and proprietary lines of Maharashtra Hybrid Seeds Company Ltd. (MHSCL)] were used in these experiments.

The seeds were surface sterilized preferably in 0.1% (weight/volume) HgCl2 in distilled water for 1 to 60 minutes (preferably 30 minutes). These seeds were washed many times in sterile distilled water and then imbibed in sterile water for 0 to 48 hours preferably 16 hrs.

The embryos were isolated from these seeds in sterile conditions by pressing to remove the seed coat with tweezers or any other means. The cotyledons were separated from embryos, and these embryos measure 1 to 8 mm preferably 5 mm long at the time of isolation. These isolated embryos were washed many times in sterile water blotted dry on filter paper and placed on soaked sterile filter paper. These embryos were wounded at the plumule tip.

B. Preparation of Transgenic *Agrobacterium tumefaciens*

The vectors used were pC 2300 which carries either Cry2Ab gene or Cry1A(c) gene and nptII gene as plant selectable marker in the T-DNA of these plasmids. One of these plasmids was introduced into the *Agrobacterium tumefaciens* strain EHA 105 and used for the transformations. The antibiotic 25 mg/l kanamycin and 10 mg/l chloramphenicol were added to 2YT medium for the selective growth of the *Agrobacterium* with the plasmid containing Cry1A(c) or Cry2Ab gene.

The *Agrobacterium* carrying either Cry2Ab or Cry1A(c) gene was used in the transformations.

C. Inoculation of Explants with Recombinant *Agrobacterium tumefaciens*

These wounded embryos were inoculated in *Agrobacterium* suspension (preferably 15 minutes), blotted dry on sterile filter paper and later transferred in petri dishes (preferably 20 embryos per petri dish) on [MS0 medium contains MS salts (Murashige and skoog., Physiol. Plant. (1962) 15:473-497, B5 vitamins (Gamborg et al., Exp. Cell Res. (1968) 50:151-158) 0.8% agar, 3% sucrose and pH 5.8].

After 2 to 4 days of co-cultivation (preferably 2 days of co-cultivation) these explants were washed in liquid MS0 medium (liquid MS0 medium contains MS salts, B5 vitamins, 3% sucrose and pH 5.8) with 500 mg/l Cefotaxime to kill the *Agrobacterium* and were transferred on $MS0Z_2K_{50}C$ medium ($MS0Z_2K_{50}C$ contains MS salts, B5 vitamins, 3% sucrose, 0.8% agar, pH 5.8, 0.05 to 5 mg/l Zeatin (preferably 2 mg/l Zeatin) supplemented with Kanamycin preferably 50 mg/l Kanamycin) and preferably 500 mg/l Cefotaxime (any other antibiotic) to kill the *Agrobacterium*). 5 to 20 developing embryos (preferably 10 embryos) were incubated per petri dish and were transferred onto fresh medium after a period of 2 to 5 weeks (preferably 3 weeks).

In a period of 3 to 7 weeks on $MS0Z_2K_{50}C$ medium, multiple shoot buds developed from the plumule of the embryo.

These multiple shoot buds were sub cultured on MS0 $K_{50}C$ ($MS0K_{50}C$ contains MS salts, B5 vitamins, 3% sucrose, 0.8% agar and adjusted the pH 5.8 supplemented with 50 mg/l Kanamycin and 500 mg/l Cefotaxime) medium at the interval of 3 weeks. These shoot bud clumps were separated by cutting and subcultured on same media for 2 to 5 weeks to develop shoots of size 0.5 cm to 5 cm preferably 1.5 cm. The said shoots were transferred onto MS0 $K_{50}C$ medium in bottles for further elongation and rooting. After 2 to 4 weeks in the rooting medium, the shoots were elongated further and the roots were well developed.

The rooted plants were hardened and established in green house. Rooted plants were tested by ELISA. Three transgenic plants were generated from 175 explants used in this transformation experiment.

Example No. 5

*Agrobacterium*-Mediated Transformation of Cotyledon Explants Using Cry1A(c) and NPT II Genes for the Generation of Insect Resistant Transgenic Okra (Marker Based System, Cocultivation on $MS0Z_2As$ Medium)

Okra genotypes representing a variety of agronomic varieties or hybrids [including Arka Anamika, Parbhani Kranti and proprietary lines of Maharashtra Hybrid Seeds Company Ltd. (MHSCL)] were used in these experiments.

The seeds were surface sterilized preferably in 0.1% (weight/volume) $HgCl_2$ in distilled water for 1 to 60 minutes (preferably 30 minutes). These seeds were washed many times in sterile distilled water.

The surface sterilized seeds were inoculated on MS0 medium in bottles and incubated under light for the germination of seeds. The cotyledon with petiole explants were excised from seedlings (1 to 20 days old seedlings preferably from 12 days old seedlings). These explants were inoculated in the *Agrobacterium* strain EHA 105 with the vector pC 2300 which carries Cry1A(c) gene and nptII gene. These explants were inoculated in *Agrobacterium* suspension (preferably 15 minutes) and transferred on $MSOZ_2As$ medium as mentioned in Example. 3. After 2 to 4 days (preferably 2 days) of cocultivation these explants were transferred on $MSOZ_2K_{50}C$ medium.

From the cut ends of the petiole of these cotyledon explants multiple shoot buds and callus developed. The shoot buds produced from the petiole of these explants were separated and subcultured on $MS0 K_{50}C$ medium for the further elongation of the shoots and rooting. Shoots elongated and roots were well developed in rooting medium during a period of 2 to 4 weeks. The rooted plants were hardened and established in green house. These plants were tested by ELISA for the presence of Cry1A(c) protein as in Example. 3. The plants were negative for the presence of Cry1A(c) protein. The calli produced from cut ends of the petiole of these explants were subcultured at an interval of 2 to 5 weeks on $MS0Z_2KC$ medium. On subculture these calli were grown in size. The pieces of calli were tested by ELISA as mentioned in Example 3 for the presence of Cry1A(c) protein. Out of 7 calli tested 4 were positive for the presence of Cry1A(c) protein, which proves that these calli were transgenic.

Negative Control for Transformation

Negative controls were maintained in each experiment to ensure that the kanamycin killed the growth of non transgenic growth. Cotyledon with petiole were excised as mentioned in 3.A.1 and with out inoculating in bacteria, were incubated on $MS0Z_2As$ medium for 2 days at the rate of preferably 10 embryos per plate. After 2 days, these were transferred on $MS0Z_2K_{50}C$ for 3 weeks period and sub-cultured at 3 weeks interval on $MS0Z_2K_{50}C$. But most of the multiple shoot buds bleached by the end of $5^{th}$ subculture. This proves kanamycin concentration preferably 50 mg/l was sufficient to control the non-transgenic growth of tissue to some extent in these experiments.

Example No. 6

*Agrobacterium*-Mediated, Co-Transformation of Embryos Using a Plasmid (T-DNA) Carrying Cry1A (c)/Cry2Ab etc. and Another Plasmid (T-DNA) Carrying NPT II And Gus Genes, for the Generation of Marker Free Bt Okra (Cocultivation on MS0 As Medium) *Agrobacterium tumefaciens* and the Constructs Used The method used was *Agrobacterium*-mediated, co-transformation, i.e. a single *Agrobacterium tumefaciens* strain carrying two plasmids. The *Agrobacterium* strain used was LBA 4404, carrying plasmid MH 0102 or MH 0103 and pC 2301. The plasmid MH 0102 or MH 0103 and pC 2201 carry Cry1A (c) or Cry2Ab and GUS & NPT II genes respectively.

The antibiotic 25 mg/l kanamycin and 10 mg/l chloramphenicol were added to 2YT medium for the selective growth of the *Agrobacterium* LBA4404 with the plasmids MH 0102 or MH 0103 and pC 2201. The tissue culture steps for the recovery of transgenic plants were as mentioned in Example 1.

A. Preparation of Plant Material

Okra genotypes representing a variety of agronomic varieties or hybrids [including Arka Anamika, Parbhani Kranti and proprietary lines of Maharashtra Hybrid Seeds Company Ltd. (MHSCL)] were used in these experiments.

The preparation of plant material and inoculation of explants with *Agrobacteruim*, and the tissue culture steps for the recovery of plants were as mentioned in Example 3.

These putative transgenic plants were screened by GUS assay (for the presence of marker gene) and ELISA (for the detection of Cry1A(c) or Cry2Ab protein). A total of 10 plants were positive for GUS expression (Table 7). The transgenic plants were hardened and established in green house.

GUS activity was detected by the histochemical assay using 5-bromo-4-chloro-3-indolyl-β-D-glucoronide as substrate (Jefferson et al., Proc. Natl. Acad. Sci. USA (1986) 83:8447-8451) and were incubated in 100 mM phosphate buffer (pH 7.0) containing 1 mg/ml X-gluc for overnight at 37° C. temperature.

Analysis of putative transgenic plants using double antibody sandwich ELISA was performed as per the manufacturer's instruction as mentioned in Example No 3.

TABLE NO. 7

ELISA (Bt) and GUS assay results of 10 transgenic $T_0$ generation plants generated from marker free system

| Sr. No. | Plant ID | ELISA reading | GUS result |
|---|---|---|---|
| 1 | OCM1 | 0.531 | + |
| 2 | OCM2a | 0.736 | + |
| 3 | OCM3 | 0.725 | + |
| 4 | OCM4 | 0.560 | + |
| 5 | OCM5a | 0.001 | + |
| 6 | OCM10a | 0.011 | + |
| 7 | OCM11a | 0.000 | + |
| 8 | OCM12a | 0.001 | + |
| 9 | OCM13a | 0.002 | + |
| 10 | OCM14a | 0.000 | + |
| 11 (Okra Non transgenic) | NTO1 | 0.010 | − |

TABLE NO. 8

Segregation of marker and Bt genes in $T_1$ generation plants derived from $T_0$ line No. OCM1)

| Sr. No. | Plant ID | ELISA reading | GUS result |
|---|---|---|---|
| 1 | OCM1-1 | 0.531 | + |
| 2 | OCM1-2 | 0.675 | + |
| 3 | OCM1-3 | 0.498 | + |
| 4 | OCM1-4 | 0.656 | + |
| 5 | OCM1-5 | 0.000 | + |
| 6 | OCM1-6 | 0.453 | − |
| 7 | OCM1-7 | 0.687 | + |

The marker-free transgenic plants i.e. carrying Bt gene [Cry1A(c) or Cry2Ab gene] but not the marker gene were identified in the following generations from the segregated progenies, as indicated in Table No 8.

The seeds obtained from the marker-free transgenic plants and appropriate controls were further inoculated in vitro on MS basal medium with kanamycin 50 mg/l (MS0 $K_{50}$ medium) to reconfirm the marker free status of these lines. These markers-free seedlings got bleached in 3 weeks period. Similar results were also seen for non transgenic controls. However seedlings carrying marker gene (GUS positive) continued to grow on the medium with kanamycin 50 mg/l. These results reconfirm the marker free status of these lines.

Example No. 7

Biolistic Method of Transformation of Okra Plants

A. Preparation of Plant Material

Okra (*Abelmoschus esculentus*) genotypes representing a variety of agronomic varieties or hybrids [including Arka Anamika, Parbhani Kranti and proprietary lines of Maharashtra Hybrid Seeds Company Ltd. (MHSCL)] were used in these experiments.

The seeds were surface sterilized preferably in 0.1% (weight/volume) $HgCl_2$ in distilled water (for 1 to 60 minutes, preferably 30 minutes). These mature seeds were washed many times in sterile distilled water. (Preferably, these surface sterilized seeds were imbibed in sterile water).

The embryos were isolated from these seeds in sterile conditions by pressing to remove the seed coat with tweezers or any other means. The cotyledons were separated from embryos and these embryos measure 1 to 8 mm (preferably 5 mm) long at the time of isolation. These isolated embryos were washed many times in sterile water blotted dry on filter paper. These embryos were wounded at the plumule tip.

B. Particle Bombardment of Explants Using Biolistic System.

All experiments were conducted with the Biolistic PDS-1000/He system (Sanford, TIB (1988) 6:299-302. Sanford et al., Technique J. Methods Cell Mol. Biol. (1991) 3:3-16) using tungsten or gold particles (3 mg) in the diameter of 0.1 to 3 µm. These particles were previously washed in ethanol were in aqueous suspension (50 µl) were coated with 5 to 10 µg of plasmid DNA. The procedure followed for the coating of DNA on gold was as described by Kikkert et al., Plant Cell Tissue and Organ Culture (1993) 33:221-226.

The particles were finely dispersed with an ultra sonicator (Elma Transonic 460 Lab-Line Instruments Inc., IL, USA) before bombardment.

The explants were arranged in the center of the petri plate on a tissue culture medium. Bombardment pressure in the range of 900 to 1500 PSI (preferably 1100 PSI) was used. The distance from the launching plate was in the range of 6 to 18 cm, (preferably 6 cm) were used. Various explants were used for particle bombardment. (The gold and tungsten particles were purchased from Bio-Rad Labs., 2000 Alfred Nobel Drive, Hercules, Calif. 94547 USA).

After bombardment, the explants were placed on MS0 medium for 2 to 5 days (preferably 3 days). After 2 to 5 days (preferably 3 days) these embryos were used for transient GUS assay or transferred on $MS0Z_2H_{10}$ medium [$MS0Z_2H_{10}C$ contains MS salts, B5 vitamins, 3% sucrose, 0.8% agar, pH 5.8, cytokinin preferably Zeatin in the range 0.05 to 5 mg/l, (preferably 2 mg/l Zeatin) supplemented with 5 mg/l to 100 mg/l Hygromycin B (preferably 10 mg/l Hygromycin B) and taken for the stable GUS assay.

C. Gus Assay of the Transformed Explants

GUS activity was detected by the histochemical assay using 5-bromo-4-chloro-3-indolyl-β-D-glucoronide as substrate (Jefferson et al., Proc. Natl. Acad. Sci. USA (1986) 83:8447-8451) and were incubated in 100 mM phosphate buffer (pH 7.0) containing 1 mg/ml X-gluc for overnight at 37° C. temperature.

All the types of explants showed GUS expression

ADVANTAGES

1. This invention provides plant regeneration from a variety of explants of Okra or *Abelmoschus* species.
2. The shoot bud regeneration frequency from plumule of embryo explants of Okra or *Abelmoschus* sps. is more than 80%.
3. This invention also provides methods for the further multiplication of the shoot buds.
4. This invention also provides methods for the transient expression of the transgene in high frequency using *Agrobacterium*-mediated transformation.
5. This invention also provides methods for the transient expression of the transgene in high frequency using biolistic-mediated transformation.
6. This invention also provides methods for the *Agrobacterium*-mediated genetic transformation of Okra or *Abelmoschus* species for the first time.
7. This invention also provides methods for the biolistic-mediated genetic transformation of Okra or *Abelmoschus* species for the first time.
8. This invention also provides methods for the generation of transgenic Okra or *Abelmoschus* sps with nucleotide sequences on interest.
9. This invention also provides methods for the generation of transgenic insect resistant Okra or *Abelmoschus* species.
10. This invention also provides methods for the generation of marker-free insect resistant transgenic Okra or *Abelmoschus* species.
11. This invention also provides methods for the generation of marker-free transgenic Okra or *Abelmoschus* sps, with the DNA sequences of interest.

REFERENCES

1. Herberlandt., Sber. Akad. Wiss. Wien. (1902) 111:69-92).
2. Chilton., Scientific American (1983) 248.6:36-45).
3. Mangat and Roy., Plant Science (1986) 47:57-62.
4. Roy and Mangat (Roy et al., Plant Science (1989) 60:77-82)
5. Murai et al., Science (1983) 222:476-482.
6. Fraley et al., Proc. Natl. Acad. Sci. USA (1983) 80:4803-4807
7. Lorz et al., Mol. Gen. Genet., (1985) 199:178-182.
8. Portrykus et al., Mol. Gen. Genet., (1985) 199:183-188;
9. Crossway et al., Mol. Gen. Genet., (1986) 202:179-185;
10. Klein et al., Nature (1987) 327:70-73
11. Fromm et al., Proc. Natl. Acad. Sci. USA (1985) 82:5824-5828,
12. Fromm et al., Nature (1986) 319:791-793.
13. Murai et al., Science (1983) 222:476-482.
14. Fraley et al., Proc. Natl. Acad. Sci. USA (1983) 80:4803-4807.
15. De Block et al., The EMBO Journal (1984) 3:1681-1689.
16. Horsch et al., Science (1985) 227:1229-1231.
17. Klein et al., Nature (1987) 327:70-73.
18. Klein et al., Bio/Technology (1992) 10:286-292.

19. Casas et al., Proc. Natl. Acad. Sci. USA (1993) 90: 11212-11216.
20. Yoder et al., Bio/Technology (1994) 12:263-267).
21. Komori et al., The Plant Journal (1996) 10: 165-174
22. Fischhoff et al., Bio/Technology (1987) 5:807-813.
23. Johnson et al., PNAS (1990) 86:9871-9875.
24. Murashige et al., Physiol. Plant. (1962) 15:473-497
25. Gamborg et al., Exp. Cell Res. (1968) 50:151-158).
26. Sanford, TIB (1988) 6:299-302.
27. Sanford et al., Technique J. Methods Cell Mol. Biol. (1991) 3:3-16).
28. Kikkert et al., Plant Cell Tissue and Organ Culture (1993) 33:221-226.
29. Jefferson et al., Proc. Natl. Acad. Sci. USA (1986) 83:8447-8451)

We claim:

1. A method for transforming an okra plant, okra plant cells or okra plant tissues, said method comprising:
   (a) surface sterilizing seeds of an okra plant, and optionally imbibing the seeds in water;
   (b) isolating immature or mature embryos from the seeds;
   (c) wounding the embryos at the plumule end;
   (d) co-cultivating the wounded embryos of step (c) in a medium containing a recombinant *Agrobacterium* strain which comprises a selectable marker gene, said *Agrobacterium* strain optionally further comprising DNA or RNA sequences of interest;
   (e) culturing the embryos of step (d) on a tissue culture medium comprising zeatin and a selection agent to select transformed okra plant cells or tissues;
   (f) culturing the transformed okra plant cells or tissues of step (e) on a suitable tissue culture medium comprising zeatin to obtain shoot buds; and
   (g) culturing the shoot buds of step (f) in a hormone-free rooting medium to obtain rooted transformed okra plants.

2. A method for transforming an okra plant, okra plant cells or okra plant tissues, said method comprising:
   (a) surface sterilizing seeds of an okra plant, and imbibing the seeds in water;
   (b) germinating the seeds of step (a) in a tissue culture medium to obtain seedlings;
   (c) isolating an explant comprising a cotyledon with petiole from the seedlings of step (b);
   (d) co-cultivating the explant of step (c) in a medium containing a recombinant *Agrobacterium* strain which comprises a selectable marker gene, said Agrobacterium strain optionally further comprising DNA or RNA sequences of interest;
   (e) culturing the explant of step (d) on a tissue culture medium comprising zeatin and a selection agent to select transformed okra plant cells or tissues;
   (f) culturing the transformed okra plant cells or tissues of step (e) on a suitable tissue culture medium comprising zeatin to obtain shoot buds; and
   (g) culturing the shoot buds of step (f) in a hormone-free rooting medium to obtain rooted transformed okra plants.

3. The method as claimed in claim 1 or 2, wherein said seeds are selected from different varieties or accessions of *Abelmoschus esculentus*.

4. The method as claimed in claim 1 or 2, wherein said recombinant *Agrobacterium* further comprises DNA or RNA sequences of interest.

5. The method as claimed in claim 4, wherein said DNA or RNA sequence comprises a coding or non-coding gene sequence, inclusive or not, of terminator or promoter, as an expressing or non-expressing cassette.

6. The method as claimed in claim 4, wherein said DNA or RNA sequences confer improved agronomic traits or combination of traits comprising yield, drought resistance, stress resistance, nutritional value, or inducing male sterility into the plant, cells or tissues.

7. The method as claimed in claim 4, wherein said DNA or RNA sequences confers tolerance or resistance to disease, herbicide or insects to plant, cells or tissues.

8. The method as claimed in claim 2, wherein said tissue culture medium of step (b) is MSO.

9. The method as claimed in claim 1 or 2, wherein said tissue culture medium of step (e) contains zeatin in the range of 0.01 to 5 mg/l and further contains an antibiotic or herbicide.

10. The method as claimed in claim 9, wherein said antibiotic is kanamycin in the range of 25 mg/l to 200 mg/l.

11. The method as claimed in claim 9, wherein said antibiotic is hygromycin in the range of 5 mg/l to 100 mg/l.

12. The method as claimed in claim 4, wherein said transformed shoot, plant cells and/or plant tissues contain DNA or RNA sequences, wherein said DNA or RNA sequence comprises a coding or non-coding gene sequence, inclusive or not, of terminator or promoter, as an expressing or non-expressing cassette or wherein said DNA or RNA sequences confers improved agronomic traits or combination of traits comprising yield, drought resistance, stress resistance, nutritional value, or inducing male sterility into the plant, cells or tissues.

13. The method as claimed in claim 12, wherein said DNA or RNA sequences are transferred to subsequent generations by plant breeding techniques including but not limited to crosses, wherein the subsequent generations contain the DNA or RNA sequences with or without the selectable marker gene.

14. A transformed okra plant, plant cells or tissues obtained by the method of claim 1 or 2.

15. A seed produced from the plant of claim 14, wherein said seed comprises the DNA or RNA sequences of interest, and/or comprises the selectable marker gene.

16. The transformed okra plant of claim 14, wherein said plant has traits of agronomic or non-agronomic importance.

17. The transformed okra plant of claim 14, wherein said plant is tolerant or resistant to insects.

18. The transformed okra plant of claim 14, wherein said plant is tolerant or resistant to diseases or herbicide.

19. The transformed okra plant of claim 14, wherein said plant has improved agronomic traits or combination of traits comprising yield, drought resistance, abiotic stress resistance, biotic stress resistance or nutritional value.

20. The transformed okra plant of claim 14, wherein said plant is male sterile.

21. The transformed okra plant of claim 14 which comprises the selectable marker gene, and/or comprises the DNA or RNA sequences of interest.

22. The method as claimed in claim 1 or 2, wherein said medium of step (d) is selected from the group consisting of MSO, MSOAs, MSOZ2 and MSOZ2As.

23. The method as claimed in claim 1 or 2, wherein said suitable tissue culture medium of step (f) is MSOZ2.

24. The method as claimed in claim 9, wherein said tissue culture medium of step (e) contains 2 mg/l zeatin.

25. The method as claimed in claim 1 or 2, wherein said rooting medium of step (g) is a basal MS medium with or without antibiotics.

26. The method as claimed in claim 23, wherein MSOZ2 contains zeatin in the range of 0.01 to 5 mg/l.

* * * * *